US005955650A

United States Patent [19]
Hitz

[11] Patent Number: 5,955,650
[45] Date of Patent: Sep. 21, 1999

[54] NUCLEOTIDE SEQUENCES OF CANOLA AND SOYBEAN PALMITOYL-ACP THIOESTERASE GENES AND THEIR USE IN THE REGULATION OF FATTY ACID CONTENT OF THE OILS OF SOYBEAN AND CANOLA PLANTS

[75] Inventor: William Dean Hitz, Wilmington, Del.

[73] Assignee: E. I. du Pont de Nemours and Company, Wilmington, Del.

[21] Appl. No.: 08/793,410

[22] PCT Filed: Aug. 25, 1995

[86] PCT No.: PCT/US95/10627

§ 371 Date: Feb. 24, 1997

§ 102(e) Date: Feb. 24, 1997

[87] PCT Pub. No.: WO96/06936

PCT Pub. Date: Mar. 7, 1996

Related U.S. Application Data

[63] Continuation of application No. 08/299,044, Aug. 31, 1994, abandoned.

[51] Int. Cl.$^6$ ............... C12N 5/14; C12N 15/29; C12N 15/52; C12N 15/82
[52] U.S. Cl. ............ 800/281; 435/320.1; 435/412; 435/415; 435/416; 435/419; 435/468; 435/469; 435/470; 536/23.2; 536/23.6
[58] Field of Search ................ 536/23.2, 23.6; 435/172.3, 320.1, 419, 468, 412, 469, 415, 470, 416; 800/205, DIG. 69, DIG. 29, DIG. 17, DIG. 14, DIG. 27, DIG. 63, DIG. 9, DIG. 23, DIG. 56, 281, 298, 306, 312, 322, 314, 320.1

[56] References Cited

U.S. PATENT DOCUMENTS

| | | | |
|---|---|---|---|
| 4,394,443 | 7/1983 | Weissman et al. | 435/6 |
| 5,530,186 | 6/1996 | Hitz et al. | 800/205 |
| 5,723,761 | 3/1998 | Voelker et al. | 800/205 |

FOREIGN PATENT DOCUMENTS

| | | | |
|---|---|---|---|
| 0 255 378 | 2/1988 | European Pat. Off. | C12N 15/00 |
| 0 301 749 | 2/1989 | European Pat. Off. | C12N 15/00 |
| WO 90/12084 | 10/1990 | WIPO | C12N 5/00 |
| 91/16421 | 10/1991 | WIPO | C12N 9/14 |
| WO 91/16421 | 10/1991 | WIPO | C12N 9/14 |
| 92/11373 | 7/1992 | WIPO | C12N 15/55 |
| 92/20236 | 11/1992 | WIPO | A23D 7/00 |
| 94/10288 | 5/1994 | WIPO | C12N 9/16 |
| 95/06740 | 3/1995 | WIPO | C12N 15/82 |

OTHER PUBLICATIONS

Knauf, Vic C, Reprogramming Levels of Fatty Acid Synthesis Enzymes in Developing Embryos of Rapeseed, *Journal of Cellular Biochemistry, UCLA Symposia on Molecular & Cellular Biology*, Supplement 14E, Abstract R 018, p. 266, 1990.

Ohlrogge, John B., Acyl Carrier Protein As A Probe of the Organization and Regulation of Plant Fatty Acid Synthesis, *Journal of Cellular Biochemistry, UCLA Symposia on Molecular & Cellular Biology*, Supplement 14E, Abstract R 019, p. 266, 1990.

F. Grellet et al., *Arabidopsis thaliana* systematic cDNA sequencing reveals a gene with homology with *Umbellularia californica* C12:0–ACP thioesterase, *Plant Physiol. Biochem.*, 31(4), 599–602, 1993.

P. Dormann et al., Cloning and Expression in *Escherichia coli* of a Novel Thioesterase from *Arabidopsis thaliana* Specific for Long–Chain Acyl–Acyl Carrier Proteins, *Archives of Biochemistry and Biophysics*, 316, No. 1, 612–618, 1995.

R. Topfer et al., Molecular Cloning of cDNAs or Genes Encoding Proteins Involved in *de novo* Fatty Acid Biosynthesis in Plants, *J. Plant Physiol.*, 143, 416–425, 1994.

N. Yadav et al., Genetic Manipulation to Alter Fatty Acid Profiles of Oilseed Crops, *Biochemistry and Molecular Biology of Membrane and Storage Lipids of Plants*, N. Murata and CR Somerville, eds., 60–67, 1993.

A. Jones et al., Isolation And Characterization of Two Thioesterase cDNA's From *Cuphea hookeriana*, *Plant Physiology Supplement*, 105, No. 1, 155, May 1994, Abstract 855.

A. Jones et al., Palmitoyl–Acyl Carrier Protein (ACP) Thioesterase and the Evolutionary Origin of Plant Acyl–ACP Thioesterases, *The Plant Cell*, 7, 359–371, Mar. 1995.

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Dormann P, et al. Cloning and expression in *Escherichia coli* of a novel thioesterase from *Arabidopsis thaliana* specific for long–chain acyl–acyl carrier proteins. Arch. Biochem. Biophys. 316: 612–618, Jan. 10, 1995.

Jones A, et al. Palmitoyl–acyl carrier protein (ACP) thioesterase and the evolutionary origin of plant acyl–ACP thioesterases. Plant Cell 7: 359–371, Mar. 1995.

Dormann P, et al. Cloning and expression in *Escherichia coli* of a cDNA coding for the oleoyl–acyl carrier protein thioesterase from coriander (*Coreiandrum sativum* L.), Apr. 14, 1994.

(List continued on next page.)

*Primary Examiner*—Lynette F. Smith
*Assistant Examiner*—Amy J. Nelson

[57] ABSTRACT

The preparation and use of nucleic acid fragments encoding acyl-acyl carrier protein thioesterase enzymes to modify plant lipid composition are disclosed. Also disclosed are chimeric genes incorporating such nucleic acid fragments and suitable regulatory sequences may be used to create transgenic plants with altered levels of saturated fatty acids.

33 Claims, No Drawings

OTHER PUBLICATIONS

Mattson, F.R. et al, *J. Lipid Researchi*, 26, 194–202 (1985).
Harwood, J., *Critical Reviews in Plant Sciences*, 8(1), 1–43 (1989).
Slabas, A.R. et al, *J. Exp. Bot.*, 41, Suppl. p–8–2 (1990).
van der Krol, A.R. et al, *Gene*, 72, 45–50 (1988).
Poulese, A.J. et al, *J. of Biol. Chem.*, 260, 15953–15958 (1985).
Naggert, J. et al, *J. of Biol. Chem.*, 263, 1146–1150 (1989).
Everett, N.P. et al, *Biotechnology*, 5, 1201–1204 (1987).
Hinchee, M.A.W. et al, *Biotechnology*, 6, 915–922 (1988).
Randhawa, Z.I. et al, *Biochemistry*, 26, 1365–1373 (1987).
De Block, M. et al, *Plant Physiol.*, 91, 694–701 (1989).
Christou, P. et al, *Proc. Natl. Acad. Sci.*, 86, 7500–7504 (1989).
Chee, P.P., et al, *Plant. Physiol.*, 91, 1212–1218 (1989).
Bafor, M. et al, *JAOCS*, 67(4), 217–225 (1990).
Goldberg, R.B., et al, *Cell*, 56, 149–160 (1989).
Grundy, S.M., *New England Journal of Medicine*, 314(12), 745–748 (1986).
Mensink, R.P. et al, *The Lancet*, 1, 122–125 (1987).
Keys, A. "Seven Countries: A Multivariate Analysis of Death of Coronary Heart Disease", Cambridge: Howard University Press pp. 8–16; 67–79; 248–262 (1980).
"Monounsaturates Use Said to Lower Several Major Risk Factors", *Food Chemical News*, Mar. 2, 1987, p.44.
Tanksley, S.D. et al *Biochemistry*, 7, 257–264 (1989).
McKeon, T.A. et al, *J. Biol. Chem.*, 257, 12141–12147 (1982).
Leto, T.L. et al, *Science*, 248, 727–729 (1990).
Murphy, D.J. et al, *Eur. J. Biochem.*, 142, 43–48 (1984).
Knauf, V.C., *Trends in Biotech.*, 5, 40–47 (1987).
Hühne, K. et al, *Fat Sci. Technol.*, 92(6), 232–236 (1990).
Battey, J.F. et al, *Trends in Biotech.*, 7(5), 122–126 (1989).
Bayley, S.A. et al, *Biotechnology*, 6(10), 1219–1221 (1988).

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 1688 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
ACAATTACAC TGTCTCTCTC TTTTCCAAAA TTAGGGAAAC AACAAGGACG CAAAATGACA      60

CAATAGCCCT TCTTCCCTGT TTCCAGCTTT TCTCCTTCTC TCTCTCTCCA TCTTCTTCTT     120

CTTCTTCACT CAGTCAGATC CAACTCCTCA GATAACACAA GACCAAACCC GCTTTTTCTG     180

CATTTCTAGA CTAGACGTTC TACCGGAGAA GCGACCTTAG AAATTCATTA TGGTGGCAAC     240

AGCTGCTACT TCATCATTTT TCCCTGTTAC TTCACCCTCG CCGGACTCTG GTGGAGCAGG     300

CAGCAAACTT GGTGGTGGGC CTGCAAACCT TGGAGGACTA AAATCCAAAT CTGCGTCTTC     360
```

| | | | |
|---|---|---|---|
| TGGTGGCTTG | AAGGCAAAGG | CGCAAGCCCC | TTCGAAAATT AATGGAACCA CAGTTGTTAC 420 |
| ATCTAAAGAA | AGCTTCAAGC | ATGATGATGA | TCTACCTTCG CCTCCCCCCA GAACTTTTAT 480 |
| CAACCAGTTG | CCTGATTGGA | GCATGCTTCT | TGCTGCTATC ACAACAATTT TCTTGGCCGC 540 |
| TGAAAAGCAG | TGGATGATGC | TTGATTGGAA | GCCACGGCGA CCTGACATGC TTATTGACCC 600 |
| CTTTGGGATA | GGAAAAATTG | TTCAGGATGG | TCTTGTGTTC CGTGAAAACT TTTCTATTAG 660 |
| ATCATATGAG | ATTGGTGCTG | ATCGTACCGC | ATCTATAGAA ACAGTAATGA ACCATTTGCA 720 |
| AGAAACTGCA | CTTAATCATG | TTAAAAGTGC | TGGGCTTCTT GGTGATGGCT TTGGTTCCAC 780 |
| GCCAGAAATG | TGCAAAAAGA | ACTTGATATG | GGTGGTTACT CGGATGCAGG TTGTGGTGGA 840 |
| ACGCTATCCT | ACATGGGGTG | ACATAGTTCA | AGTGGACACT TGGGTTTCTG GATCAGGGAA 900 |
| GAATGGTATG | CGTCGTGATT | GGCTTTTACG | TGACTCCAAA ACTGGTGAAA TCTTGACAAG 960 |
| AGCTTCCAGT | GTTTGGGTCA | TGATGAATAA | GCTAACACGG AGGCTGTCTA AAATTCCAGA 1020 |
| AGAAGTCAGA | CAGGAGATAG | GATCTTATTT | TGTGGATTCT GATCCAATTC TGGAAGAGGA 1080 |
| TAACAGAAAA | CTGACTAAAC | TTGACGACAA | CACAGCGGAT TATATTCGTA CCGGTTTAAG 1140 |
| TCCTAGGTGG | AGTGATCTAG | ATATCAATCA | GCATGTCAAC AATGTGAAGT ACATTGGCTG 1200 |
| GATTCTGGAG | AGTGCTCCAC | AGCCAATCTT | GGAGAGTCAT GAGCTTTCTT CCATGACTTT 1260 |
| AGAGTATAGG | AGAGAGTGTG | GTAGGACAG | TGTGCTGGAT TCCCTGACTG CTGTATCTGG 1320 |
| GGCCGACATG | GGCAATCTAG | CTCACAGCGG | GCATGTTGAG TGCAAGCATT TGCTTCGACT 1380 |
| GGAAAATGGT | GCTGAGATTG | TGAGGGGCAG | GACTGAGTGG AGGCCCAAAC CTGTGAACAA 1440 |
| CTTTGGTGTT | GTGAACCAGG | TTCCAGCAGA | AAGCACCTAA GATTTGAAAT GGTTAACGAT 1500 |
| TGGAGTTGCA | TCAGTCTCCT | TGCTATGTTT | AGACTTATTC TGGTTCCCTG GGAGAGTTT 1560 |
| TGCTTGTGTC | TATCCAATCA | ATCTACATGT | CTTTAAATAT ATACACCTTC TAATTTGTGA 1620 |
| TACTTTGGTG | GGTAAGGGGG | AAAAGCAGCA | GTAAATCTCA TTCTCATTGT AATTAAAAAA 1680 |
| AAAAAAAA | | | 1688 |

(2) INFORMATION FOR SEQ ID NO:2:

(i) SEQUENCE CHARACTERISTICS:
        (A) LENGTH: 1483 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

| | | | |
|---|---|---|---|
| GGCACGAGCT | CATTCTTCCC | TCTCCCATCT | TCCCCACTCG ACCCCACCGC AAAAACCAAC 60 |
| AAAGTCACCA | CCTCCACCAA | CTTCTCCGGC | ATCTTCCCCA CTCCAAACTC CTCCGGCAGA 120 |
| TGAAGGTTAA | ACCAAACGCT | CAGGCCCCAC | CCAAGATCAA CGGCAAGAGA GTCGGTCTCC 180 |
| CTTCTGGCTC | GGTGAAGCCT | GATAACGAGA | CGTCCTCACA GCATCCCGCA GCACCGAGGA 240 |
| CGTTCATCAA | CCAGCTGCCT | GACTGGAGCA | TGCTTCTTGC TGCAATAACA ACCGTCTTCT 300 |
| TGGCGGCTGA | GAAGCAGTGG | ATGATGCTTG | ACTGGAAACC GAGGCGCTCT GACGTGATTA 360 |
| TGGATCCGTT | TGGGTTAGGG | AGGATCGTTC | AGGATGGGCT TGTGTTCCGT CAGAATTTCT 420 |
| CTATTCGGTC | TTATGAGATA | GGTGCTGATC | GCTCTGCGTC TATAGAAACG TTATGAATC 480 |
| ATTTACAGGA | AACGGCACTA | AACCATGTTA | AGACTGCTGG ACTGCTTGGA GATGGGTTTG 540 |

```
GTTCTACTCC TGAGATGGTT AAGAAGAACT TGATTTGGGT TGTTACTCGT ATGCAGGTTG      600

TCGTTGATAA ATATCCTACT TGGGGAGATG TTGTGGAAGT AGATACATGG GTGAGCCAGT      660

CTGGAAAGAA CGGTATGCGT CGTGATTGGC TAGTTCGAGA TGGCAATACT GGAGAAATTT      720

TAACAAGAGC ATCAAGTGTG TGGGTGATGA TGAATAAACT GACAAGAAGA TTATCAAAGA      780

TTCCTGAAGA GGTTCGAGGG GAGATAGAGC CTTACTTTGT TAATTCTGAC CCAGTCCTTG      840

CCGAGGACAG CAGAAAGTTA ACAAAACTTG ATGACAAGAC TGCTGACTAT GTTCGTTCTG      900

GTCTCACTCC GCGTTGGAGT GACTTGGATG TTAACCAGCA CGTTAACAAT GTGAAGTACA      960

TCGGGTGGAT ACTGGAGAGT GCACCTGTGG GGATGATGGA GAGTCAGAAG CTGAAAAGCA     1020

TGACTCTGGA GTATCGCAGG GAGTGCGGGA GGGACAGTGT GCTTCAGTCC CTCACCGCGG     1080

TTTCGGGCTG CGATATCGGT AGCCTCGGGA CGGCTGGTGA AGTGGAATGT CAGCATCTGC     1140

TCCGTCTCCA GGATGGAGCT GAAGTGGTGA GAGGAAGAAC AGAGTGGAGT TCCAAAACAT     1200

CAACAACAAC TTGGGACATC ACACCGTGAA AAGAATATAG CAAACATGGG TTCTTTGGTT     1260

CGTTTGTAAA ACTATACTAC CTTGCTTGCA ACCACCACTA CTCAAAAACA GTTTGGGCCA     1320

CCTTTGTATA TTTTCTTTGG TTCTTATTTT TTTTCTTCTT GGAGGTCCCT TTTTATTATA     1380

TTTATTTTTT CTTTTGGGTG CCAGACAAAG GCAAATAACT TTCTTATCCT AATATTATTT     1440

AAATGTATTT TATTTTGGGG GTTTAAAAAA AAAAAAAAAA AAA                       1483
```

(2) INFORMATION FOR SEQ ID NO:3:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
CATGGAGGAG CAG                                                         13
```

(2) INFORMATION FOR SEQ ID NO:4:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
CTGCTCCTC                                                               9
```

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

AAGGAAAAAA GCGGCCGCTG ACACAATAGC CCTTCT                        36

(2) INFORMATION FOR SEQ ID NO:6:

(i) SEQUENCE CHARACTERISTICS:
        (A) LENGTH: 328 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO:6:

```
Met Glu Glu Gln Leu Pro Asp Trp Ser Met Leu Leu Ala Ala Ile Thr
 1               5                  10                  15

Thr Val Phe Leu Ala Ala Glu Lys Gln Trp Met Met Leu Asp Trp Lys
             20                  25                  30

Pro Arg Arg Ser Asp Val Ile Met Asp Pro Phe Gly Leu Gly Arg Ile
         35                  40                  45

Val Gln Asp Gly Leu Val Phe Arg Gln Asn Phe Ser Ile Arg Ser Tyr
     50                  55                  60

Glu Ile Gly Ala Asp Arg Ser Ala Ser Ile Glu Thr Val Met Asn His
65                  70                  75                  80

Leu Gln Glu Thr Ala Leu Asn His Val Lys Thr Ala Gly Leu Leu Gly
                 85                  90                  95

Asp Gly Phe Gly Ser Thr Pro Glu Met Val Lys Lys Asn Leu Ile Trp
            100                 105                 110

Val Val Thr Arg Met Gln Val Val Asp Lys Tyr Pro Thr Trp Gly
        115                 120                 125

Asp Val Val Glu Val Asp Thr Trp Val Ser Gln Ser Gly Lys Asn Gly
    130                 135                 140

Met Arg Arg Asp Trp Leu Val Arg Asp Gly Asn Thr Gly Glu Ile Leu
145                 150                 155                 160

Thr Arg Ala Ser Ser Val Trp Val Met Met Asn Lys Leu Thr Arg Arg
                165                 170                 175

Leu Ser Lys Ile Pro Glu Glu Val Arg Gly Glu Ile Glu Pro Tyr Phe
            180                 185                 190

Val Asn Ser Asp Pro Val Leu Ala Glu Asp Ser Arg Lys Leu Thr Lys
        195                 200                 205

Leu Asp Asp Lys Thr Ala Asp Tyr Val Arg Ser Gly Leu Thr Pro Arg
    210                 215                 220

Trp Ser Asp Leu Asp Val Asn Gln His Val Asn Asn Val Lys Tyr Ile
225                 230                 235                 240

Gly Trp Ile Leu Glu Ser Ala Pro Val Gly Met Met Glu Ser Gln Lys
                245                 250                 255

Leu Lys Ser Met Thr Leu Glu Tyr Arg Arg Glu Cys Gly Arg Asp Ser
            260                 265                 270

Val Leu Gln Ser Leu Thr Ala Val Ser Gly Cys Asp Ile Gly Ser Leu
        275                 280                 285

Gly Thr Ala Gly Glu Val Glu Cys Gln His Leu Leu Arg Leu Gln Asp
```

```
                    290                 295                 300
Gly Ala Glu Val Val Arg Gly Arg Thr Glu Trp Ser Ser Lys Thr Ser
305                 310                 315                 320

Thr Thr Thr Trp Asp Ile Thr Pro
                325
```

(2) INFORMATION FOR SEQ ID NO:7:

(i) SEQUENCE CHARACTERISTICS:
        (A) LENGTH: 328 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO:7:

```
Met Glu Glu Gln Leu Ala Ala Ile Thr Thr Ile Phe Leu Ala Ala
1               5                   10                  15

Glu Lys Gln Trp Met Met Leu Asp Trp Lys Pro Arg Arg Pro Asp Met
                20                  25                  30

Leu Ile Asp Pro Phe Gly Ile Gly Lys Ile Val Gln Asp Gly Leu Val
                35                  40                  45

Phe Arg Glu Asn Phe Ser Ile Arg Ser Tyr Glu Ile Gly Ala Asp Arg
50                  55                  60

Thr Ala Ser Ile Glu Thr Val Met Asn His Leu Gln Glu Thr Ala Leu
65                  70                  75                  80

Asn His Val Lys Ser Ala Gly Leu Leu Gly Asp Gly Phe Gly Ser Thr
                85                  90                  95

Pro Glu Met Cys Lys Lys Asn Leu Ile Trp Val Val Thr Arg Met Gln
                100                 105                 110

Val Val Glu Arg Tyr Pro Thr Trp Gly Asp Ile Val Gln Val Asp
                115                 120                 125

Thr Trp Val Ser Gly Ser Gly Lys Asn Gly Met Arg Arg Asp Trp Leu
130                 135                 140

Leu Arg Asp Ser Lys Thr Gly Glu Ile Leu Thr Arg Ala Ser Ser Val
145                 150                 155                 160

Trp Val Met Met Asn Lys Leu Thr Arg Arg Leu Ser Lys Ile Pro Glu
                165                 170                 175

Glu Val Arg Gln Glu Ile Gly Ser Tyr Phe Val Asp Ser Asp Pro Ile
                180                 185                 190

Leu Glu Glu Asp Asn Arg Lys Leu Thr Lys Leu Asp Asp Asn Thr Ala
                195                 200                 205

Asp Tyr Ile Arg Thr Gly Leu Ser Pro Arg Trp Ser Asp Leu Asp Ile
210                 215                 220

Asn Gln His Val Asn Asn Val Lys Tyr Ile Gly Trp Ile Leu Glu Ser
225                 230                 235                 240

Ala Pro Gln Pro Ile Leu Glu Ser His Glu Leu Ser Ser Met Thr Leu
                245                 250                 255

Glu Tyr Arg Arg Glu Cys Gly Arg Asp Ser Val Leu Asp Ser Leu Thr
                260                 265                 270

Ala Val Ser Gly Ala Asp Met Gly Asn Leu Ala His Ser Gly His Val
                275                 280                 285

Glu Cys Lys His Leu Leu Arg Leu Glu Asn Gly Ala Glu Ile Val Arg
                290                 295                 300
```

```
Gly Arg Thr Glu Trp Arg Pro Lys Pro Val Asn Asn Phe Gly Val Val
305                 310                 315                 320

Asn Gln Val Pro Ala Glu Ser Thr
                325
```

(2) INFORMATION FOR SEQ ID NO:8:

(i) SEQUENCE CHARACTERISTICS:
        (A) LENGTH: 1174 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
ATAGGAGGTG GGAGAATGGG TATAGAATAA CATCAATGGC AGCAACTGCG GATCAAGCAG      60
CTTTCATATT AAGCATACCA AAGCGTAAGA TGGTGGATGA AACTCAAGAG ACTCTCCGCA     120
CCACCGCCTT TCCAAGTACT CATGTCAAGG TTGGTTTCTT TAGCTTTGAA CACAGATTTG     180
GATCTTTTTG TTTTGTTTCC ATATACTTAG GACCTGAGAG CTTTTGGTTG ATTTTTTTTT     240
CAGGACAAAT GGGCGAAGAA TCTGTACATT GCATCAATAT GCTATGGCAG GACAGTGTGC     300
TGATACACAC TTAAGCATCA TGTGGAAAGC CAAAGACAAT TGGAGCGAGA CTCAGGGTCG     360
TCATAATACC AATCAAAGAC GTAAAACCAG ACGCAACCTC TTTGGTTGAA TGTAATGAAA     420
GGGATGTGTC TTGGTATGTA TGTACGAATA ACAAAAGAGA AGATGGAATT AGTAGTAGAA     480
AATATTTGGG AGCTTTTTAA GCCCTTCAAG TGTGCTTTTT ATCTTATTGA TATCATCCAT     540
TTGCGTTGTT TAATGCGTCT CTAGATATGT TCCTATATCT TTCTCAGTGT CTGATAAGTG     600
AAATGTGAGA AAACCATACC AAACCAAAAT ATTCAAATCT TATTTTTAAT AATGTTGAAT     660
CACTCGGAGT TGCCACCTTC TGTGCCAATT GTGCTGAATC TATCACACTA GAAAAAAACA     720
TTTCTTCAAG GTAATGACTT GTGGACTATG TTCTGAATTC TCATTAAGTT TTTATTTTCT     780
GAAGTTTAAG TTTTTACCTT CTGTTTTGAA ATATATCGTT CATAAGATGT CACGCCAGGA     840
CATGAGCTAC ACATCGCACA TAGCATGCAG ATCAGGACGA TTTGTCACTC ACTTCAAACA     900
CCTAAGAGCT TCTCTCTCAC AGCGCACACA CATATGCATG CAATATTTAC ACGTGATCGC     960
CATGCAAATC TCCATTCTCA CCTATAAATT AGAGCCTCGG CTTCACTCTT TACTCAAACC    1020
AAAACTCATC ACTACAGAAC ATACACAAAT GGCGAACAAG CTCTTCCTCG TCTCGGCAAC    1080
TCTCGCCTTG TTCTTCCTTC TCACCAATGC CTCCGTCTAC AGGACGGTTG TGGAAGTCGA    1140
CGAAGATGAT GCCACAAATC CAGCCGGCCC ATTT                                1174
```

(2) INFORMATION FOR SEQ ID NO:9:

(i) SEQUENCE CHARACTERISTICS:
        (A) LENGTH: 1174 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
TATCCTCCAC CCTCTTACCC ATATCTTATT GTAGTTACCG TCGTTGACGC CTAGTTCGTC      60

GAAAGTATAA TTCGTATGGT TTCGCATTCT ACCACCTACT TTGAGTTCTC TGAGAGGCGT     120

GGTGGCGGAA AGGTTCATGA GTACAGTTCC AACCAAAGAA ATCGAAACTT GTGTCTAAAC     180

CTAGAAAAAC AAAACAAAGG TATATGAATC CTGGACTCTC GAAAACCAAC TAAAAAAAAA     240

GTCCTGTTTA CCCGCTTCTT AGACATGTAA CGTAGTTATA CGATACCGTC CTGTCACACG     300

ACTATGTGTG AATTCGTAGT ACACCTTTCG GTTTCTGTTA ACCTCGCTCT GAGTCCCAGC     360

AGTATTATGG TTAGTTTCTG CATTTTGGTC TGCGTTGGAG AAACCAACTT ACATTACTTT     420

CCCTACACAG AACCATACAT ACATGCTTAT TGTTTTCTCT TCTACCTTAA TCATCATCTT     480

TTATAAACCC TCGAAAAATT CGGGAAGTTC ACACGAAAAA TAGAATAACT ATAGTAGGTA     540

AACGCAACAA ATTACGCAGA GATCTATACA AGGATATAGA AAGAGTCACA GACTATTCAC     600

TTTACACTCT TTTGGTATGG TTTGTTTTA TAAGTTTAGA ATAAAAATTA TTACAACTTA     660

GTGAGCCTCA ACGGTGGAAG ACACGGTTAA CACGACTTAG ATAGTGTGAT CTTTTTTTGT     720

AAAGAAGTTC CATTACTGAA CACCTGATAC AAGACTTAAG AGTAATTCAA AAATAAAAGA     780

CTTCAAATTC AAAAATGGAA GACAAAACTT TATATAGCAA GTATTCTACA GTGCGGTCCT     840

GTACTCGATG TGTAGCGTGT ATCGTACGTC TAGTCCTGCT AAACAGTGAG TGAAGTTTGT     900

GGATTCTCGA AGAGAGAGTG TCGCGTGTGT GTATACGTAC GTTATAAATG TGCACTAGCG     960

GTACGTTTAG AGGTAAGAGT GGATATTTAA TCTCGGAGCC GAAGTGAGAA ATGAGTTTGG    1020

TTTTGAGTAG TGATGTCTTG TATGTGTTTA CCGCTTGTTC GAGAAGGAGC AGAGCCGTTG    1080

AGAGCGGAAC AAGAAGGAAG AGTGGTTACG GAGGCAGATG TCCTGCCAAC ACCTTCAGCT    1140

GCTTCTACTA CGGTGTTTAG GTCGGCCGGG TAAA                                1174

(2) INFORMATION FOR SEQ ID NO:10:

(i) SEQUENCE CHARACTERISTICS:
        (A) LENGTH:  1303 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (iv) ANTI-SENSE:  NO (xi) SEQUENCE DESCRIPTION:  SEQ ID NO:10:

ACGCACTTAC CTAGAGCTTG CAACATCAGG CAAGTTAGCA TTTGCCCCTT CCAGAAGACC      60

ATGCCTGGGC CCGGCTTCTA CTAGATTCCA AACGAATATC CTCGAGAGTG TGTATACCAC     120

GGTGATATGA GTGTGGTTGT TGATGTATGT TAACACTACA TAGTCATGGT GTGTGTTCCA     180

TAAATAATGT ACTAATGTAA TAAGAACTAC TCCGTAGACG GTAATAAAAG AGAAGTTTTT     240

TTTTTTTACT CTTGCTACTT TCCTATAAAG TGATGATTAA CAACAGATAC ACCAAAAAGA     300

AAACAATTAA TCTATATTCA CAATGAAGCA GTACTAGTCT ATTGAACATG TCAGATTTTC     360

TTTTTCTAAA TGTCTAATTA AGCCTTCAAG GCTAGTGATG ATAAAAGATC ATCCAATGGG     420

ATCCAACAAA GACTCAAATC TGGTTTTGAT CAGATACTTC AAAACTATTT TTGTATTCAT     480

TAAATTATGC AAGTGTTCTT TTATTTGGTG AAGACTCTTT AGAAGCAAAG AACGACAAGC     540

AGTAATAAAA AAAACAAAGT TCAGTTTTAA GATTTGTTAT TGACTTATTG TCATTTGAAA     600

AATATAGTAT GATATTAATA TAGTTTTATT TATATAATGC TTGTCTATTC AAGATTTGAG     660

AACATTAATA TGATACTGTC CACATATCCA ATATATTAAG TTTCATTTCT GTTCAAACAT     720
```

```
ATGATAAGAT GGTCAAATGA TTATGAGTTT TGTTATTTAC CTGAAGAAAA GATAAGTGAG    780
CTTCGAGTTT CTGAAGGGTA CGTGATCTTC ATTTCTTGGC TAAAAGCGAA TATGACATCA    840
CCTAGAGAAA GCCGATAATA GTAAACTCTG TTCTTGGTTT TTGGTTTAAT CAAACCGAAC    900
CGGTAGCTGA GTGTCAAGTC AGCAAACATC GCAAACCATA TGTCAATTCG TTAGATTCCC    960
GGTTTAAGTT GTAAACCGGT ATTTCATTTG GTGAAACCC TAGAAGCCAG CCACCTTTTT    1020
AATCTAATTT TTGCAAACGA GAAGTCACCA CACCTCTCCA CTAAAACCCT GAACCTTACT   1080
GAGAGAAGCA GAGCAAAAGA ACAAATAAAA CCCGAAGATG AGACCACCAC GTGCGGCGGG   1140
ACGTTCAGGG GACGGGGAGG AAGAGAATGC GGCGGTTTGG TGGCGGCGGC GGACGTTTGG   1200
TGGCGGCGGT GGACGTTTTG GTGGCGGCGG TGGACCTTTG GTGGTGGATA TCGTGACGAA   1260
GGACCTCCCA GTGAAGTCAT TGGTTCGTTT ACTCTTTTCT TAG                     1303
```

(2) INFORMATION FOR SEQ ID NO:11:

(i) SEQUENCE CHARACTERISTICS:
        (A) LENGTH: 1303 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

```
TGCGTGAATG GATCTCGAAC GTTGTAGTCC GTTCAATCGT AAACGGGGAA GGTCTTCTGG     60
TACGGACCCG GGCCGAAGAT GATCTAAGGT TTGCTTATAG GAGCTCTCAC ACATATGGTG    120
CCACTATACT CACACCAACA ACTACATACA ATTGTGATGT ATCAGTACCA CACACAAGGT    180
ATTTATTACA TGATTACATT ATTCTTGATG AGGCATCTGC CATTATTTTC TCTTCAAAAA    240
AAAAAAATGA GAACGATGAA AGGATATTTC ACTACTAATT GTTGTCTATG TGGTTTTTCT    300
TTTGTTAATT AGATATAAGT GTTACTTCGT CATGATCAGA TAACTTGTAC AGTCTAAAAG    360
AAAAAGATTT ACAGATTAAT TCGGAAGTTC CGATCACTAC TATTTTCTAG TAGGTTACCC    420
TAGGTTGTTT CTGAGTTTAG ACCAAAACTA GTCTATGAAG TTTTGATAAA AACATAAGTA    480
ATTTAATACG TTCACAAGAA AATAAACCAC TTCTGAGAAA TCTTCGTTTC TTGCTGTTCG    540
TCATTATTTT TTTTGTTTCA AGTCAAAATT CTAAACAATA ACTGAATAAC AGTAAACTTT    600
TTATATCATA CTATAATTAT ATCAAAATAA ATATATTACG AACAGATAAG TTCTAAACTC    660
TTGTAATTAT ACTATGACAG GTGTATAGGT TATATAATTC AAAGTAAAGA CAAGTTTGTA    720
TACTATTCTA CCAGTTTACT AATACTCAAA ACAATAAATG GACTTCTTTT CTATTCACTC    780
GAAGCTCAAA GACTTCCCAT GCACTAGAAG TAAAGAACCG ATTTTCGCTT ATACTGTAGT    840
GGATCTCTTT CGGCTATTAT CATTTGAGAC AAGAACCAAA AACCAAATTA GTTTGGCTTG    900
GCCATCGACT CACAGTTCAG TCGTTTGTAG CGTTTGGTAT ACAGTTAAGC AATCTAAGGG    960
CCAAATTCAA CATTTGGCCA TAAAGTAAAC CACTTTTGGG ATCTTCGGTC GGTGGAAAAA   1020
TTAGATTAAA AACGTTTGCT CTTCAGTGGT GTGGAGAGGT GATTTGGGA CTTGGAATGA   1080
CTCTCTTCGT CTCGTTTTCT TGTTTATTTT GGGCTTCTAC TCTGGTGGTG CACGCCGCCC   1140
TGCAAGTCCC CTGCCCCTCC TTCTCTTACG CCGCCAAACC ACCGCCGCCG CCTGCAAACC   1200
ACCGCCGCCA CCTGCAAAAC CACCGCCGCC ACCTGGAAAC CACCACCTAT AGCACTGCTT   1260
```

```
CCTGGAGGGT CACTTCAGTA ACCAAGCAAA TGAGAAAAGA ATC              1303
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

```
AAGGAAAAAA GCGGCCGCGA TTTACTGCTG CTTTTC                      36
```

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

```
AACATCAATG GCAGCAACTG CGGA                                   24
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

```
GCCGGCTGGA TTTGTGGCAT CAT                                    23
```

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

```
CTAGATCTCC ATGGGTGTAT GTTCTGTAGT GATG                        34
```

(2) INFORMATION FOR SEQ ID NO:16:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

TCAGGCCTGT CGACCTGCGG ATCAAGCAGC TTTCA                                    35

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

CTAGATCTGG TACCTAGATT CCAAACGAAA TCCT                                     34

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

AACATCAGGC AAGTTAGCAT TTGC                                                24

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

TCAGGCCTGT CGACGAGGTC CTTCGTCAGC ATAT                                     34

(2) INFORMATION FOR SEQ ID NO:20:

(i) SEQUENCE CHARACTERISTICS:
        (A) LENGTH: 24 base pairs
        (B) TYPE: nucleic acid

```
          (C) STRANDEDNESS:  single
          (D) TOPOLOGY:  linear (ii) MOLECULE TYPE:  DNA (genomic)

(iii) HYPOTHETICAL:  NO (iv) ANTI-SENSE:  NO (xi) SEQUENCE DESCRIPTION:  SEQ ID NO:20:

AACGAACCAA TGACTTCACT GGGA                                                  24

(2) INFORMATION FOR SEQ ID NO:21:

(i) SEQUENCE CHARACTERISTICS:
          (A) LENGTH:  36 base pairs
          (B) TYPE:  nucleic acid
          (C) STRANDEDNESS:  single
          (D) TOPOLOGY:  linear (ii) MOLECULE TYPE:  DNA (genomic)

(iii) HYPOTHETICAL:  NO (iv) ANTI-SENSE:  NO (xi) SEQUENCE DESCRIPTION:  SEQ ID NO:21:

CCATGGGAGC TCGTCGACGA GGTCCTTCGT CACGAT                                     36

(2) INFORMATION FOR SEQ ID NO:22:

(i) SEQUENCE CHARACTERISTICS:
          (A) LENGTH:  36 base pairs
          (B) TYPE:  nucleic acid
          (C) STRANDEDNESS:  single
          (D) TOPOLOGY:  linear (ii) MOLECULE TYPE:  DNA (genomic)

(iii) HYPOTHETICAL:  NO (iv) ANTI-SENSE:  NO (xi) SEQUENCE DESCRIPTION:  SEQ ID NO:22:

GAGCTCCCAT GGAGATCTGG TACCTAGATT CCAAAC                                     36

(2) INFORMATION FOR SEQ ID NO:23:

(i) SEQUENCE CHARACTERISTICS:
          (A) LENGTH:  20 base pairs
          (B) TYPE:  nucleic acid
          (C) STRANDEDNESS:  single
          (D) TOPOLOGY:  linear (ii) MOLECULE TYPE:  DNA (genomic)

(iii) HYPOTHETICAL:  NO (iv) ANTI-SENSE:  NO (xi) SEQUENCE DESCRIPTION:  SEQ ID NO:23:

GACTATGTTC TGAATTCTCA                                                       20

(2) INFORMATION FOR SEQ ID NO:24:

(i) SEQUENCE CHARACTERISTICS:
          (A) LENGTH:  39 base pairs
          (B) TYPE:  nucleic acid
          (C) STRANDEDNESS:  single
          (D) TOPOLOGY:  linear (ii) MOLECULE TYPE:  DNA (genomic)
```

(iii) HYPOTHETICAL: NO (iv) ANTI-SENSE: NO (xi) SEQUENCE DESCRIPTION: SEQ ID NO:24:

GACAAGATCT GCGGCCGCTA AAGAGTGAAG CCGAGGCTC                39

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

GTCGACGAGG                                               10

(2) INFORMATION FOR SEQ ID NO:26:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

AGATCTGGTA CC                                            12

(2) INFORMATION FOR SEQ ID NO:27:

(i) SEQUENCE CHARACTERISTICS:
        (A) LENGTH: 1688 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:27:

TTTTTTTTTT TTTTAATTAC AATGAGAATG AGATTTACTG CTGCTTTTCC CCCTTACCCA       60

CCAAAGTATC ACAAATTAGA AGGTGTATAT ATTTAAAGAC ATGTAGATTG ATTGGATAGA      120

CACAAGCAAA ACTCTCCCCA GGGAACCAGA ATAAGTCTAA ACATAGCAAG GAGACTGATG      180

CAACTCCAAT CGTTAACCAT TTCAAATCTT AGGTGCTTTC TGCTGGAACC TGGTTCACAA      240

CACCAAAGTT GTTCACAGGT TTGGGCCTCC ACTCAGTCCT GCCCCTCACA ATCTCAGCAC      300

CATTTTCCAG TCGAAGCAAA TGCTTGCACT CAACATGCCC GCTGTGAGCT AGATTGCCCA      360

TGTCGGCCCC AGATACAGCA GTCAGGGAAT CCAGCACACT GTCCCTACCA CACTCTCTCC      420

TATACTCTAA AGTCATGGAA GAAAGCTCAT GACTCTCCAA GATTGGCTGT GGAGCACTCT      480

```
CCAGAATCCA GCCAATGTAC TTCACATTGT TGACATGCTG ATTGATATCT AGATCACTCC    540

ACCTAGGACT TAAACCGGTA CGAATATAAT CCGCTGTGTT GTCGTCAAGT TTAGTCAGTT    600

TTCTGTTATC CTCTTCCAGA ATTGGATCAG AATCCACAAA ATAAGATCCT ATCTCCTGTC    660

TGACTTCTTC TGGAATTTTA GACAGCCTCC GTGTTAGCTT ATTCATCATG ACCCAAACAC    720

TGGAAGCTCT TGTCAAGATT TCACCAGTTT TGGAGTCACG TAAAAGCCAA TCACGACGCA    780

TACCATTCTT CCCTGATCCA GAAACCCAAG TGTCCACTTG AACTATGTCA CCCCATGTAG    840

GATAGCGTTC CACCACAACC TGCATCCGAG TAACCACCCA TATCAAGTTC TTTTTGCACA    900

TTTCTGGCGT GGAACCAAAG CCATCACCAA GAAGCCCAGC ACTTTTAACA TGATTAAGTG    960

CAGTTTCTTG CAAATGGTTC ATTACTGTTT CTATAGATGC GGTACGATCA GCACCAATCT   1020

CATATGATCT AATAGAAAAG TTTTCACGGA ACACAAGACC ATCCTGAACA ATTTTTCCTA   1080

TCCCAAAGGG GTCAATAAGC ATGTCAGGTC GCCGTGGCTT CCAATCAAGC ATCATCCACT   1140

GCTTTTCAGC GGCCAAGAAA ATTGTTGTGA TAGCAGCAAG AAGCATGCTC CAATCAGGCA   1200

ACTGGTTGAT AAAAGTTCTG GGGGAGGCG AAGGTAGATC ATCATCATGC TTGAAGCTTT   1260

CTTTAGATGT AACAACTGTG GTTCCATTAA TTTTCGAAGG GGCTTGCGCC TTTGCCTTCA   1320

AGCCACCAGA AGACGCAGAT TTGGATTTTA GTCCTCCAAG GTTTGCAGGC CCACCACCAA   1380

GTTTGCTGCC TGCTCCACCA GAGTCCGGCG AGGGTGAAGT AACAGGGAAA AATGATGAAG   1440

TAGCAGCTGT TGCCACCATA ATGAATTTCT AAGGTCGCTT CTCCGGTAGA ACGTCTAGTC   1500

TAGAAATGCA GAAAAGCGG GTTTGGTCTT GTGTTATCTG AGGAGTTGGA TCTGACTGAG   1560

TGAAGAAGAA GAAGAAGATG GAGAGAGAGA GAAGGAGAAA AGCTGGAAAC AGGGAAGAAG   1620

GGCTATTGTG TCATTTTGCG TCCTTGTTGT TTCCCTAATT TTGGAAAAGA GAGAGACAGT   1680

GTAATTGT                                                            1688

(2) INFORMATION FOR SEQ ID NO:28:

(i) SEQUENCE CHARACTERISTICS:
        (A) LENGTH:  1483 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (iv) ANTI-SENSE:  YES (xi) SEQUENCE DESCRIPTION:  SEQ ID NO:28:

TTTTTTTTTT TTTTTTTTA AACCCCCAAA ATAAAATACA TTTAAATAAT ATTAGGATAA     60

GAAAGTTATT TGCCTTTGTC TGGCACCCAA AGAAAAAAT AAATATAATA AAAAGGGACC    120

TCCAAGAAGA AAAAAAATAA GAACCAAAGA AAATATACAA AGGTGGCCCA AACTGTTTTT   180

GAGTAGTGGT GGTTGCAAGC AAGGTAGTAT AGTTTTACAA ACGAACCAAA GAACCCATGT   240

TTGCTATATT CTTTTCACGG TGTGATGTCC CAAGTTGTTG TTGATGTTTT GGAACTCCAC   300

TCTGTTCTTC CTCTCACCAC TTCAGCTCCA TCCTGGAGAC GGAGCAGATG CTGACATTCC   360

ACTTCACCAG CCGTCCCGAG GCTACCGATA TCGCAGCCCG AAACCGCGGT GAGGGACTGA   420

AGCACACTGT CCCTCCCGCA CTCCCTGCGA TACTCCAGAG TCATGCTTTT CAGCTTCTGA   480

CTCTCCATCA TCCCCACAGG TGCACTCTCC AGTATCCACC CGATGTACTT CACATTGTTA   540

ACGTGCTGGT TAACATCCAA GTCACTCCAA CGCGGAGTGA GACCAGAACG AACATAGTCA   600

GCAGTCTTGT CATCAAGTTT TGTTAACTTT CTGCTGTCCT CGGCAAGGAC TGGGTCAGAA   660
```

```
TTAACAAAGT AAGGCTCTAT CTCCCCTCGA ACCTCTTCAG GAATCTTTGA TAATCTTCTT    720

GTCAGTTTAT TCATCATCAC CCACACACTT GATGCTCTTG TTAAAATTTC TCCAGTATTG    780

CCATCTCGAA CTAGCCAATC ACGACGCATA CCGTTCTTTC CAGACTGGCT CACCCATGTA    840

TCTACTTCCA CAACATCTCC CCAAGTAGGA TATTTATCAA CGACAACCTG CATACGAGTA    900

ACAACCCAAA TCAAGTTCTT CTTAACCATC TCAGGAGTAG AACCAAACCC ATCTCCAAGC    960

AGTCCAGCAG TCTTAACATG GTTTAGTGCC GTTTCCTGTA AATGATTCAT AACCGTTTCT   1020

ATAGACGCAG AGCGATCAGC ACCTATCTCA TAAGACCGAA TAGAGAAATT CTGACGGAAC   1080

ACAAGCCCAT CCTGAACGAT CCTCCCTAAC CCAAACGGAT CCATAATCAC GTCAGAGCGC   1140

CTCGGTTTCC AGTCAAGCAT CATCCACTGC TTCTCAGCCG CCAAGAAGAC GGTTGTTATT   1200

GCAGCAAGAA GCATGCTCCA GTCAGGCAGC TGGTTGATGA ACGTCCTCGG TGCTGCGGGA   1260

TGCTGTGAGG ACGTCTCGTT ATCAGGCTTC ACCGAGCCAG AAGGGAGACC GACTCTCTTG   1320

CCGTTGATCT TGGGTGGGGC CTGAGCGTTT GGTTTAACCT TCATCTGCCG GAGGAGTTTG   1380

GAGTGGGGAA GATGCCGGAG AAGTTGGTGG AGGTGGTGAC TTTGTTGGTT TTTGCGGTGG   1440

GGTCGAGTGG GGAAGATGGG AGAGGGAAGA ATGAGCTCGT GCC                    1483
```

(2) INFORMATION FOR SEQ ID NO:29:

(i) SEQUENCE CHARACTERISTICS:
        (A) LENGTH: 324 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO:29:

```
Leu Pro Asp Trp Ser Met Leu Leu Ala Ala Ile Thr Thr Val Phe Leu
1               5                   10                  15

Ala Ala Glu Lys Gln Trp Met Met Leu Asp Trp Lys Pro Arg Arg Ser
            20                  25                  30

Asp Val Ile Met Asp Pro Phe Gly Leu Gly Arg Ile Val Gln Asp Gly
        35                  40                  45

Leu Val Phe Arg Gln Asn Phe Ser Ile Arg Ser Tyr Glu Ile Gly Ala
    50                  55                  60

Asp Arg Ser Ala Ser Ile Glu Thr Val Met Asn His Leu Gln Glu Thr
65                  70                  75                  80

Ala Leu Asn His Val Lys Thr Ala Gly Leu Leu Gly Asp Gly Phe Gly
                85                  90                  95

Ser Thr Pro Glu Met Val Lys Lys Asn Leu Ile Trp Val Val Thr Arg
            100                 105                 110

Met Gln Val Val Val Asp Lys Tyr Pro Thr Trp Gly Asp Val Val Glu
        115                 120                 125

Val Asp Thr Trp Val Ser Gln Ser Gly Lys Asn Gly Met Arg Arg Asp
    130                 135                 140

Trp Leu Val Arg Asp Gly Asn Thr Gly Glu Ile Leu Thr Arg Ala Ser
145                 150                 155                 160

Ser Val Trp Val Met Met Asn Lys Leu Thr Arg Arg Leu Ser Lys Ile
                165                 170                 175

Pro Glu Glu Val Arg Gly Glu Ile Glu Pro Tyr Phe Val Asn Ser Asp
            180                 185                 190
```

```
Pro Val Leu Ala Glu Asp Ser Arg Lys Leu Thr Lys Leu Asp Asp Lys
            195                 200                 205

Thr Ala Asp Tyr Val Arg Ser Gly Leu Thr Pro Arg Trp Ser Asp Leu
210                 215                 220

Asp Val Asn Gln His Val Asn Asn Val Lys Tyr Ile Gly Trp Ile Leu
225                 230                 235                 240

Glu Ser Ala Pro Val Gly Met Met Glu Ser Gln Lys Leu Lys Ser Met
                245                 250                 255

Thr Leu Glu Tyr Arg Arg Glu Cys Gly Arg Asp Ser Val Leu Gln Ser
            260                 265                 270

Leu Thr Ala Val Ser Gly Cys Asp Ile Gly Ser Leu Gly Thr Ala Gly
            275                 280                 285

Glu Val Glu Cys Gln His Leu Leu Arg Leu Gln Asp Gly Ala Glu Val
            290                 295                 300

Val Arg Gly Arg Thr Glu Trp Ser Ser Lys Thr Ser Thr Thr Thr Trp
305                 310                 315                 320

Asp Ile Thr Pro (2) INFORMATION FOR SEQ ID NO:30:

(i) SEQUENCE CHARACTERISTICS:
        (A) LENGTH:  324 amino acids
        (B) TYPE:  amino acid
        (C) STRANDEDNESS:  unknown
        (D) TOPOLOGY:  unknown (ii) MOLECULE TYPE:  protein (iii) HYPOTHETICAL:  NO (xi) SEQUENCE DESCRIPTION:  SEQ ID NO:30:

Leu Leu Ala Ala Ile Thr Thr Ile Phe Leu Ala Ala Glu Lys Gln Trp
1               5                   10                  15

Met Met Leu Asp Trp Lys Pro Arg Arg Pro Asp Met Leu Ile Asp Pro
                20                  25                  30

Phe Gly Ile Gly Lys Ile Val Gln Asp Gly Leu Val Phe Arg Glu Asn
            35                  40                  45

Phe Ser Ile Arg Ser Tyr Glu Ile Gly Ala Asp Arg Thr Ala Ser Ile
50                  55                  60

Glu Thr Val Met Asn His Leu Gln Glu Thr Ala Leu Asn His Val Lys
65                  70                  75                  80

Ser Ala Gly Leu Leu Gly Asp Gly Phe Gly Ser Thr Pro Glu Met Cys
                85                  90                  95

Lys Lys Asn Leu Ile Trp Val Val Thr Arg Met Gln Val Val Val Glu
                100                 105                 110

Arg Tyr Pro Thr Trp Gly Asp Ile Val Gln Val Asp Thr Trp Val Ser
            115                 120                 125

Gly Ser Gly Lys Asn Gly Met Arg Arg Asp Trp Leu Leu Arg Asp Ser
            130                 135                 140

Lys Thr Gly Glu Ile Leu Thr Arg Ala Ser Ser Val Trp Val Met Met
145                 150                 155                 160

Asn Lys Leu Thr Arg Arg Leu Ser Lys Ile Pro Glu Glu Val Arg Gln
                165                 170                 175

Glu Ile Gly Ser Tyr Phe Val Asp Ser Asp Pro Ile Leu Glu Glu Asp
            180                 185                 190

Asn Arg Lys Leu Thr Lys Leu Asp Asp Asn Thr Ala Asp Tyr Ile Arg
            195                 200                 205
```

```
    Thr Gly Leu Ser Pro Arg Trp Ser Asp Leu Asp Ile Asn Gln His Val
        210                 215                 220
    Asn Asn Val Lys Tyr Ile Gly Trp Ile Leu Glu Ser Ala Pro Gln Pro
    225                 230                 235                 240
    Ile Leu Glu Ser His Glu Leu Ser Ser Met Thr Leu Glu Tyr Arg Arg
                    245                 250                 255
    Glu Cys Gly Arg Asp Ser Val Leu Asp Ser Leu Thr Ala Val Ser Gly
                260                 265                 270
    Ala Asp Met Gly Asn Leu Ala His Ser Gly His Val Glu Cys Lys His
            275                 280                 285
    Leu Leu Arg Leu Glu Asn Gly Ala Glu Ile Val Arg Gly Arg Thr Glu
        290                 295                 300
    Trp Arg Pro Lys Pro Val Asn Asn Phe Gly Val Val Asn Gln Val Pro
    305                 310                 315                 320
    Ala Glu Ser Thr
```

(2) INFORMATION FOR SEQ ID NO:31:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:31:

```
GCACGAGCTC GTGCCGAATT CGGCACGAGC GGCACGAGGA AAATACAGAG AGACAAATTT      60

AAAACAAAAC GAAAGGAGAT CGAGAGAGGA GAGAGGCGCA CACACACACA CACAAAGGAG     120

AACTTTAGGG TTTGGGGAGA CTCCGAAGAG ATTGGCGTAA CACTTCTGTC TTTGAACGCT     180

TATCTTCCTC GTCATGGTGG CTACTTGCGC TACGTCGTCG TTTTTTCATG TTCCATCTTC     240

TTCCTCGCTT GATACGAATG GGAAGGGGAA CAGAGTTGGG TCCACTAATT TTGCTGGACT     300

TAACTCAACG CCAAGCTCTG GGAGGATGAA GGTTAAGCCA AACGCTCAGG CTCCACCCAA     360

GATCAACGGG AAGAAAGCTA ACTTGCCTGG CTCTGTAGAG ATATCAAAGG CTGACAACGA     420

GACTTCGCAG CCCGCACACG CACCGAGGAC GTTTATCAAC CAGCTGCCTG ACTGGAGTAT     480

GCTGCTTGCT GCTATAACTA CCATTTTCTT GGCAGCGGAG AAACAGTGGA TGATGCTTGA     540

CTGGAAACCG AGGCGTTCTG ATATGATTAT GGATCCTTTT GGTTTAGGGA GAATTGTTCA     600

GGATGGTCTT GTGTTCCGTC AGAATTTTTC CATTAGGTCT TATGAAATAG GTGCTGATCG     660

CTCTGCGTCT ATAGAAACTG TCATGAATCA TTTACAGGAA ACGGCGCTTA ATCATGTGAA     720

GTCTGCCGGA CTGCTGGAAA ATGGGTTTGG GTCCACTCCT GAGATGTTTA AGAAGAATTT     780

GATATGGGTC GTTGCTCGTA TGCAGGTTGT CGTTGATAAA TATCCTACTT GGGGAGATGT     840

TGTGGAAGTG GATACTTGGG TTAGTCAGTC TGGAAAGAAT GGTATGCGTC GTGATTGGCT     900

AGTTCGGGAT TGCAATACTG GAGAAATTGT AACGCGAGCA TCAAGTTTGT GGGTGATGAT     960

GAATAAACTC ACAAGGAGAT TGTCAAAGAT TCCTGAAGAG GTTCGAGGGG AAATAGAGCC    1020

TTATTTTGTG AACTCTGATC CTGTCATTGC CGAAGACAGC AGAAAGTTAA CAAAACTTGA    1080

TGACAAGACT GCTGACTATG TTCGTTCTGG TCTCACTCCG AGGTGGAGTG ACTTGGATGT    1140

TAACCAGCAT GTTAACAATG TAAAGTACAT TGGGTGGATA CTGGAGAGTG CTCCAGCAGG    1200

GATGCTGGAG AGTCAGAAGC TGAAAAGCAT GACTCTGGAG TATCGCAGGG AGTGCGGGAG    1260
```

-continued

```
AGACAGTGTG CTTCAGTCTC TCACCGCAGT CTCTGGATGT GATGTCGGTA ACCTCGGGAC    1320

AGCCGGGGAA GTGGAGTGTC AGCATTTGCT TCGACTCCAG GATGGAGCTG AAGTGGTGAG    1380

AGGAAGAACA GAGTGGAGCT CCAAGACAGG AGCAACAACT TGGGACACTA CTACATCGTA    1440

AACATTGGTC CTTTGGTTCC TTTGTAAAAC TGTACCTGCT GCTACCTTCT TGCAACCACC    1500

ACCTTTGTAT ATTTCTTCTT TTTTGTTTTT TATTTTGCTT CAATGGAGAT ATATTATTAT    1560

TTATTTAATC TTTCTATTTT TTTTGTTTTC TTATGGGAAA TGGGTGTATT ATGTGATATA    1620

TTATTGTAAC CCCATGTGCC AGGGCAAGGC AATAACTTTC TTATCAAAAA AAAA          1674
```

(2) INFORMATION FOR SEQ ID NO: 32:

(i) SEQUENCE CHARACTERISTICS:
        (A) LENGTH: 415 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 32:

```
Met Val Ala Thr Cys Ala Thr Ser Ser Phe Phe His Val Pro Ser Ser
1               5                   10                  15

Ser Ser Leu Asp Thr Asn Gly Lys Gly Asn Arg Val Gly Ser Thr Asn
            20                  25                  30

Phe Ala Gly Leu Asn Ser Thr Pro Ser Ser Gly Arg Met Lys Val Lys
        35                  40                  45

Pro Asn Ala Gln Ala Pro Pro Lys Ile Asn Gly Lys Lys Ala Asn Leu
    50                  55                  60

Pro Gly Ser Val Glu Ile Ser Lys Ala Asp Asn Glu Thr Ser Gln Pro
65                  70                  75                  80

Ala His Ala Pro Arg Thr Phe Ile Asn Gln Leu Pro Asp Trp Ser Met
                85                  90                  95

Leu Leu Ala Ala Ile Thr Thr Ile Phe Leu Ala Ala Glu Lys Gln Trp
            100                 105                 110

Met Met Leu Asp Trp Lys Pro Arg Arg Ser Asp Met Ile Met Asp Pro
        115                 120                 125

Phe Gly Leu Gly Arg Ile Val Gln Asp Gly Leu Val Phe Arg Gln Asn
    130                 135                 140

Phe Ser Ile Arg Ser Tyr Glu Ile Gly Ala Asp Arg Ser Ala Ser Ile
145                 150                 155                 160

Glu Thr Val Met Asn His Leu Gln Glu Thr Ala Leu Asn His Val Lys
                165                 170                 175

Ser Ala Gly Leu Leu Glu Asn Gly Phe Gly Ser Thr Pro Glu Met Phe
            180                 185                 190

Lys Lys Asn Leu Ile Trp Val Ala Arg Met Gln Val Val Val Asp
        195                 200                 205

Lys Tyr Pro Thr Trp Gly Asp Val Val Glu Val Asp Thr Trp Val Ser
    210                 215                 220

Gln Ser Gly Lys Asn Gly Met Arg Arg Asp Trp Leu Val Arg Asp Cys
225                 230                 235                 240

Asn Thr Gly Glu Ile Val Thr Arg Ala Ser Ser Leu Trp Val Met Met
                245                 250                 255

Asn Lys Leu Thr Arg Arg Leu Ser Lys Ile Pro Glu Glu Val Arg Gly
            260                 265                 270
```

-continued

```
Glu Ile Glu Pro Tyr Phe Val Asn Ser Asp Pro Val Ile Ala Glu Asp
    275                 280                 285

Ser Arg Lys Leu Thr Lys Leu Asp Asp Lys Thr Ala Asp Tyr Val Arg
    290                 295                 300

Ser Gly Leu Thr Pro Arg Trp Ser Asp Leu Asp Val Asn Gln His Val
305                 310                 315                 320

Asn Asn Val Lys Tyr Ile Gly Trp Ile Leu Glu Ser Ala Pro Ala Gly
                325                 330                 335

Met Leu Glu Ser Gln Lys Leu Lys Ser Met Thr Leu Glu Tyr Arg Arg
            340                 345                 350

Glu Cys Gly Arg Asp Ser Val Leu Gln Ser Leu Thr Ala Val Ser Gly
        355                 360                 365

Cys Asp Val Gly Asn Leu Gly Thr Ala Gly Glu Val Glu Cys Gln His
    370                 375                 380

Leu Leu Arg Leu Gln Asp Gly Ala Glu Val Val Arg Gly Arg Thr Glu
385                 390                 395                 400

Trp Ser Ser Lys Thr Gly Ala Thr Thr Trp Asp Thr Thr Ser
                405                 410                 415
```

NUCLEOTIDE SEQUENCES OF CANOLA AND SOYBEAN PALMITOYL-ACP THIOESTERASE GENES AND THEIR USE IN THE REGULATION OF FATTY ACID CONTENT OF THE OILS OF SOYBEAN AND CANOLA PLANTS

This application is a 371 of PCT/US95/10627 filed Aug. 25, 1995 which is a continuation of U.S. application Ser. No. 08/299,044, filed Aug. 31, 1994, now abandoned.

FIELD OF INVENTION

The invention relates to the preparation and use of nucleic acid fragments encoding acyl-acyl carrier protein thioesterase enzymes to modify plant lipid composition. Chimeric genes incorporating such nucleic acid fragments and suitable regulatory sequences may be used to create transgenic plants with altered levels of saturated fatty acids.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of saturation of the lipid.

Plant lipids find their major use as edible oils in the form of triacylglycerols. The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids. The relative amounts of saturated and unsaturated fatty acids in commonly used, edible vegetable oils are summarized below (Table 1):

TABLE 1

Percentages of Saturated and Unsaturated Fatty Acids in the Oils of Selected Oil Crops

|           | Saturated | Mono-unsaturated | Poly-unsaturated |
|-----------|-----------|------------------|------------------|
| Canola    | 6%        | 58%              | 36%              |
| Soybean   | 15%       | 24%              | 61%              |
| Corn      | 13%       | 25%              | 62%              |
| Peanut    | 18%       | 48%              | 34%              |
| Safflower | 9%        | 13%              | 78%              |
| Sunflower | 9%        | 41%              | 51%              |
| Cotton    | 30%       | 19%              | 51%              |

Many recent research efforts have examined the role that saturated and unsaturated fatty acids play in reducing the risk of coronary heart disease. In the past, it was believed that mono-unsaturates, in contrast to saturates and poly-unsaturates, had no effect on serum cholesterol and coronary heart disease risk. Several recent human clinical studies suggest that diets high in mono-unsaturated fat and low in saturated fat may reduce the "bad" (low-density lipoprotein) cholesterol while maintaining the "good" (high-density lipoprotein) cholesterol (Mattson et al., *Journal of Lipid Research* (1985) 26:194–202). Soybean oil is high in saturated fatty acids when compared to other sources of vegetable oil and contains a low proportion of oleic acid, relative to the total fatty acid content of the soybean seed. These characteristics do not meet important health needs as defined by the American Heart Association.

A soybean oil low in total saturates and polyunsaturates and high in monounsaturate would provide significant health benefits to the United States population, as well as, economic benefit to oil processors.

Oil biosynthesis in plants has been fairly well-studied [see Harwood (1989) in *Critical Reviews in Plant Sciences*, Vol. 8 (1):1–43]. The biosynthesis of palmitic, stearic and oleic acids occur in the plastids by the interplay of three key enzymes of the "ACP track": palmitoyl-ACP elongase, stearoyl-ACP desaturase and the acyl-ACP thioesterases.

Of these three enzyme types, the acyl-ACP thioesterases function to remove the acyl chain from the carrier protein (ACP) and thus from the metabolic pathway. The oleoy-ACP thioesterase catalyzes the hydrolysis of oleoyl-ACP thioesters at high rates and at much lower rates the hydrolysis of palmitoyl-ACP and stearoyl-ACP. This multiple activity leads to substrate competition between enzymes and it is the competition of this acyl-ACP thioesterase and palmitoyl-ACP elongase for the same substrate and of acyl-ACP thioesterase and stearoyl-ACP desaturase for the same substrate that leads to a portion of the production of the palmitic and stearic acids found in the triacylglyceride of vegetable oils.

Once removed from the ACP track fatty acids are exported to the cytoplasm and there used to synthesize acyl-coenzyme A. These acyl-CoA's are the acyl donors for at least three different glycerol acylating enzymes (glycerol-3-P acyltransferase, 1-acyl-glycerol-3-P acyltransferase and diacylglycerol acyltransferase) which incorporate the acyl moieties into triacylglycerides during oil biosynthesis.

These acyltransferases show a strong, but not absolute, preference for incorporating saturated fatty acids at positions 1 and 3 and monounsaturated fatty acid at position 2 of the triglyceride. Thus, altering the fatty acid composition of the acyl pool will drive by mass action a corresponding change in the fatty acid composition of the oil.

Based on the above discussion, one approach to altering the levels of palmitic, stearic and oleic acids in vegetable oils is by altering their levels in the cytoplasmic acyl-CoA pool used for oil biosynthesis.

In previous work (WO 9211373) Applicant has demonstrated that oleoyl-ACP thioesterase may be modulated using cloned cDNA encoding the soybean enzyme. Oleoyl-ACP thioesterase cDNA was used to form chimeric genes for the transformation of soybean plant cells resulting in the anti-sense inhibition of acyl-ACP thioesterase in the plant seed.

Applicant has now discovered an entirely new plant thioesterase with activity on a C16 substrate that is also useful for the regulation of the acyl coenzyme A pool. Applicant has isolated nucleic acid fragments that encode soybean and canola palmitoyl-ACP thioesterases that are useful in modifying fatty acid composition in oil-producing species by genetic transformation. Thus, transfer of the nucleic acid fragments of the invention or a part thereof that encodes a functional enzyme, along with suitable regulatory sequences that direct the transcription of their mRNA, into a living cell will result in the production or over-production of palmitoyl-ACP thioesterases and will result in increased levels of saturated fatty acids in cellular lipids, including triacylglycerols.

Transfer of the nucleic acid fragments of the invention or a part thereof, along with suitable regulatory sequences that direct the transcription of their anti-sense RNA, into plants will result in the inhibition of expression of the endogenous palmitoyl-ACP thioesterase that is substantially homologous with the transferred nucleic acid fragment and will result in decreased levels of saturated fatty acids in cellular lipids, including triacylglycerols.

Transfer of the nucleic acid fragments of the invention or a part thereof, along with suitable regulatory sequences that direct the transcription of their mRNA, into plants may result in inhibition by cosuppression of the expression of the endogenous palmitoyl-ACP thioesterase gene that is substantially homologous with the transferred nucleic acid fragment and may result in decreased levels of unsaturated fatty acids in cellular lipids, including triacylglycerols.

SUMMARY OF THE INVENTION

A means to control the levels of saturated and unsaturated fatty acids in edible plant oils has been discovered. Utilizing the soybean seed palmitoyl-ACP thioesterase cDNA, for either the precursor or enzyme, chimeric genes are created and may be utilized to transform soybean plants to produce seed oils with reduced levels of saturated fatty acids. Similarly the canola seed palmitoyl-ACP thioesterase cDNA for either the precursor or enzyme may be utilized to create chimeric genes and these genes may then be used to transform canola plants to produce seed oils with reduced levels of saturated fatty acids.

Specifically, one aspect of the present invention is a nucleic acid fragment comprising a nucleotide sequence encoding the soybean seed palmitoyl-ACP thioesterase cDNA corresponding to nucleotides 1 to 1688 in the sequence shown in Sequence Description SEQ ID NO:1, or any nucleic acid fragment substantially homologous therewith. In addition, another aspect involves a nucleic acid fragment comprising a nucleotide sequence encoding the canola seed palmitoyl-ACP thioesterase cDNA corresponding to the nucleotides 1 to 1488 in the Sequence Description SEQ ID NO:2, nucleotides 1 to 1674 in the Sequence Description SEQ ID NO:31 or any nucleic acid fragment substantially homologous therewith. Preferred are those nucleic acid fragments encoding the soybean seed palmitoyl-ACP thioesterase precursor, the mature soybean seed palmitoyl-ACP thioesterase enzyme, the canola seed palmitoyl-ACP thioesterase precursor, and the mature canola seed palmitoyl-ACP thioesterase enzyme.

Another aspect of this invention involves a chimeric gene capable of transforming a soybean plant cell comprising a nucleic acid fragment encoding the soybean seed palmitoyl-ACP thioesterase cDNA of Sequence ID 1 operably linked to suitable regulatory sequences producing anti-sense inhibition of soybean seed palmitoyl-ACP thioesterase in the seed or linked suitably to produce sense expression of the soybean seed palmitoyl-ACP thioesterase gene resulting in either over expression of the palmitoyl-ACP thioesterase protein or under expression of the palmitoyl-ACP thioesterase protein when co-suppression occurs. Preferred are those chimeric genes which incorporate nucleic acid fragments encoding soybean seed palmitoyl-ACP thioesterase precursor or mature soybean seed palmitoyl-ACP thioesterase enzyme.

Yet another embodiment of the invention involves a method of producing seed oil containing either elevated or reduced levels of saturated fatty acids comprising: (a) transforming a soybean plant cell with a chimeric gene described above, (b) growing sexually mature plants from said transformed plant cells, (c) screening progeny seeds from said sexually mature plants for the desired levels of palmitic and stearic acid, and (d) crushing said progeny seed to obtain said oil containing decreased levels of palmitic and stearic acid. Preferred methods of transforming such plant cells would include the use of Ti and Ri plasmids of Agrobacterium, electroporation, and high-velocity ballistic bombardment.

Another aspect of this invention involves a chimeric gene capable of transforming a canola plant cell comprising a nucleic acid fragment encoding the canola seed palmitoyl-ACP thioesterase cDNA of Sequence ID 2 or Sequence ID 31 operably linked to suitable regulatory sequences producing anti-sense inhibition of canola seed palmitoyl-ACP thioesterase in the seed or linked suitably to produce sense expression of the canola seed palmitoyl-ACP thioesterase gene resulting in either over expression of the palmitoyl-ACP thioesterase protein or under expression of the palmitoyl-ACP thioesterase protein when co-suppression occurs. Preferred are those chimeric genes which incorporate nucleic acid fragments encoding canola seed palmitoyl-ACP thioesterase precursor or mature canola seed palmitoyl-ACP thioesterase enzyme.

BRIEF DESCRIPTION OF THE SEQUENCES

The invention can be more fully understood from the following detailed description and the Sequence Descriptions which form a part of this application.

The sequence descriptions summarize the Sequences Listing attached hereto. The Sequence Listing contains one letter codes for nucleotide sequence characters and the three letter codes for amino acids as defined in the IUPAC-IUB standards described in *Nucleic Acids Research* 13:3021–3030 (1985) and in the *Biochemical Journal* 219 (No. 2):345–373 (1984), and the symbols and format used for all nucleotide and amino acid sequence data further comply with the rules governing nucleotide and/or amino acid sequence disclosures in patent applications as set forth in 37 C.F.R. §1.821–1.825.

SEQ ID NO:1 sets forth the nucleotide sequence of a soybean palmitoyl-ACP thioesterase cDNA.

SEQ ID NO:2 sets forth the nucleotide sequence of a canola palmitoyl-ACP thioesterase cDNA.

SEQ ID NOS:3 and 4 set forth the sequence of oligonucleotides used to form a linker.

SEQ ID NO:5 sets forth the sequence of an oligonucleotide primer derived from SEQ ID NO: 1.

SEQ ID NO:6 sets forth the deduced sequence of the protein expressed in *E. coli* from the canola cDNA set forth in SEQ ID NO:2.

SEQ ID NO:7 is the deduced sequence of the protein expressed in *E. coli* from the soybean cDNA set forth in SEQ ID NO:1.

SEQ ID NO:8 sets forth the nucleotide sequence of the napin promoter used to drive seed-specific expression of thioesterase in canola.

SEQ ID NO:9 sets forth the complement of the sequence of SEQ ID NO:8.

SEQ ID NO:10 sets forth the sequence derived from the napin gene 3' of the coding region.

SEQ ID NO:11 sets forth the complement of the sequence of SEQ ID NO:10.

SEQ ID NO:12 sets forth the sequence of an oligonucleotide primer derived from SEQ ID NO:1.

SEQ ID NOS:13 through 20 set forth the sequences of oligonucleotide primers used to amplify segments of the napin promoter.

SEQ ID NOS:21 and 22 set forth the sequences of oligonucleotide primers used to amplify segments of the napin terminator region.

SEQ ID NOS:23 and 24 set forth the sequences of oligonucleotide primers used to amplify a segment from the 3' end of the napin promoter.

SEQ ID NOS:25 and 26 set forth short sequences of DNA that were introduced into the PCR amplified version of the napin terminator.

SEQ ID NO:27 sets forth the reverse complement of the soybean cDNA sequence of SEQ ID NO:1.

SEQ ID NO:28 sets forth the reverse complement of the canola cDNA sequence of SEQ ID NO:2.

SEQ ID NO:29 sets forth the predicted amino acid sequence encoded by the sequence of SEQ ID NO:1.

SEQ ID NO:30 sets forth the predicted amino acid sequence encoded by the sequence of SEQ ID NO:2.

SEQ ID NO:31 sets forth the nucleotide sequence of a second canola palmitoyl-ACP thioesterase cDNA.

SEQ ID NO:32 sets forth the predicted amino acid sequence encoded by the sequence of SEQ ID NO:31.

DETAILED DESCRIPTION OF THE INVENTION

In the context of this disclosure, a number of terms shall be used.

Fatty acids are specified by the number of carbon atoms and the number and position of the double bond: the numbers before and after the colon refer to the chain length and the number of double bonds, respectively. The number following the fatty acid designation indicates the position of the double bond from the carboxyl end of the fatty acid with the "c" affix for the cis-configuration of the double bond. For example, palmitic acid (16:0), stearic acid (18:0), oleic acid (18:1,9c), petroselinic acid (18:1, 6c), linoleic acid (18:2, 9c,12c), g-linolenic acid (18:3, 6c,9c,12c) and a-linolenic acid (18:3, 9c,12c,15c). Unless otherwise specified 18:1, 18:2 and 18:3 refer to oleic, linoleic and linolenic fatty acids. The term "palmitoyl-ACP thioesterase" used herein refers to an enzyme which catalyzes the hydrolytic cleavage of the carbon-sulfur thioester bond in the pantothene prosthetic group of palmitoyl-acyl carrier protein as its preferred reaction. Hydrolysis of other fatty acid-acyl carrier protein thioesters may also be catalyzed by the enzymes. The term "nucleic acid" refers to a large molecule which can be single-stranded or double-stranded, composed of monomers (nucleotides) containing a sugar, a phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to the sequence of DNA or RNA polymers, which can be single- or double-stranded, optionally containing synthetic, non-natural or altered nucleotide bases capable of incorporation into DNA or RNA polymers. The term "oligomer" refers to short nucleotide sequences, usually up to 100 bases long. As used herein, the term "homologous to" refers to the relatedness between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.); or by the comparison of sequence similarity between two nucleic acids or proteins, such as by the method of Needleman et al. (J. Mol. Biol. (1970) 48:443–453). As used herein, "substantially homologous" refers to nucleotide sequences that have more than 90% overall identity at the nucleotide level with the coding region of the claimed sequence, such as genes and pseudo-genes corresponding to the coding regions. The nucleic acid fragments described herein include molecules which comprise possible variations, both man-made and natural, such as but not limited to (a) those that involve base changes that do not cause a change in an encoded amino acid, or (b) which involve base changes that alter an amino acid but do not affect the functional properties of the protein encoded by the DNA sequence, (c) those derived from deletions, rearrangements, amplifications, random or controlled mutagenesis of the nucleic acid fragment, and (d) even occasional nucleotide sequencing errors.

"Gene" refers to a nucleic acid fragment that expresses a specific protein, including regulatory sequences preceding (5' non-coding) and following (3' non-coding) the coding region. "Native" gene refers to an isolated gene with its own regulatory sequences as found in nature. "Chimeric gene" refers to a gene that comprises heterogeneous regulatory and coding sequences not found in nature. "Endogenous" gene refers to the native gene normally found in its natural location in the genome and is not isolated. A "foreign" gene refers to a gene not normally found in the host organism but that is introduced by gene transfer. "Pseudo-gene" refers to a genomic nucleotide sequence that does not encode a functional enzyme.

"Coding sequence" refers to a DNA sequence that codes for a specific protein and excludes the non-coding sequences. It may constitute an "uninterrupted coding sequence", i.e., lacking an intron or it may include one or more introns bounded by appropriate splice junctions. An "intron" is a nucleotide sequence that is transcribed in the primary transcript but that is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the coding sequence uninterrupted by introns between initiation and termination codons that encodes an amino acid sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases.

As used herein, "suitable regulatory sequences" refer to nucleotide sequences in native or chimeric genes that are located upstream (5'), within, and/or downstream (3') to the nucleic acid fragments of the invention, which control the expression of the nucleic acid fragments of the invention. The term "expression", as used herein, refers to the transcription and stable accumulation of the sense (mRNA) or the antisense RNA derived from the nucleic acid fragment(s) of the invention that, in conjunction with the protein apparatus of the cell, results in altered levels of the palmitoyl-ACP thioesterase. Expression or overexpression of the gene involves transcription of the gene and translation of the mRNA into precursor or mature palmitoyl-ACP thioesteras proteins. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a foreign gene which has substantial homology to an endogenous gene resulting in the suppression of expression of both the foreign and the endogenous gene. "Altered levels" refers to the production of gene product(s) in transgenic organisms in amounts or proportions that differ from that of normal or non-transformed organisms.

"Promoter" refers to a DNA sequence in a gene, usually upstream (5') to its coding sequence, which controls the expression of the coding sequence by providing the recognition for RNA polymerase and other factors required for proper transcription. In artificial DNA constructs promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively.

The "3' non-coding sequences" refers to the DNA sequence portion of a gene that contains a poly-adenylation signal and any other regulatory signal capable of affecting mRNA processing or gene expression. The polyadenylation signal is usually characterized by affecting the addition of polyadenylic acid tracts to the 3' end of the mRNA precursor.

"Transformation" herein refers to the transfer of a foreign gene into the genome of a host organism and its genetically stable inheritance. "Restriction fragment length polymorphism" refers to different sized restriction fragment lengths due to altered nucleotide sequences in or around variant forms of genes. "Fertile" refers to plants that are able to propagate sexually.

"Plants" refer to photosynthetic organisms, both eukaryotic and prokaryotic, whereas the term "Higher plants" refers to eukaryotic plants. "Oil-producing species" herein refers to plant species which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling Brassica species, and *Arabidopsis thaliana*, and wild species which may be a source of unique fatty acids.

"Sequence-dependent protocols" refer to techniques that rely on a nucleotide sequence for their utility. Examples of sequence-dependent protocols include, but are not limited to, the methods of nucleic acid and oligomer hybridization and methods of DNA and RNA amplification such as are exemplified in various uses of the polymerase chain reaction (PCR).

"PCR" or "polymerase chain reaction" will refer to a method that results in the linear or logarithmic amplification of nucleic acid molecules. PCR generally requires a replication composition consisting of, for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.).

The present invention describes two nucleic acid fragments that encode soybean and canola seed palmitoyl-ACP thioesterases. These enzymes catalyze the hydrolytic cleavings of palmitic acid, stearic acid and oleic acid from ACP in the respective acyl-ACPs. Transfer of one or both of these nucleic acid fragments of the invention or a part thereof that encodes a functional enzyme, with suitable regulatory sequences into a living cell will result in the production or over-production of palmitoly-ACP thioesterase, which may result in increased levels of palmitic and to a lesser extent, stearic acids in cellular lipids, including oil.

Transfer of the nucleic acid fragment or fragments of the invention, with suitable regulatory sequences that transcribe the present cDNA, into a plant which has an endogenous seed palmitoyl-ACP thioesterase that is substantially homogeneous with the present cDNA may result in inhibition by co-suppresion of the expression of the endogenous palmitoyl-ACP thioesterase gene and, consequently, in a decreased amount of palmitic and to a lesser extent stearic acids in the seed oil.

Transfer of the nucleic acid fragment or fragments of the invention into a soybean or canola plants with suitable regulatory sequences that transcribe the anti-sense RNA complementary to the mRNA, or its precursor, for seed palmitoyl-ACP thioesterase may result in the inhibition of the expression of the endogenous palmitoyl-ACP thioesterase gene and, consequently, in reduced amounts of palmitic and to a lesser extent stearic acids in the seed oil.

The nucleic acid fragments of the invention can also be used as a restriction fragment length polymorphism markers in soybean and canola genetic studies and breeding programs.

Identification and Isolation of Soybean and Canola Palmitoyl-ACP Thioesterase Coding cDNA In order to identify cDNA encoding for palmitoyl-ACP thioesterase in both soybean and canola it was first necessary to construct a probe suitable for screening cDNA libraries from these plant genomes. A portion of the Arabidopis cDNA known to have significant homology with an Umbellularia C12:0-ACP thioesterase was used to design PCR primers (SEQ ID NO:3 and 4). Polysomal RNA was isolated and purified from Arabidopis and used as a template for RNA-PCR (GeneAmp® PNA-PCR kit Perkin Elmer Cetus, part number N808-0017). Using this method a 560 bp fragment was generated, and radiolabeled to be used as a probe for screening soybean and canola cDNA libraries.

Methods of creating cDNA libraries from eukaryotic genomes are well known in the art (see, for example, Sambrook, et al. (Molecular Cloning, A Laboratory Manual, 2nd ed. (1989), Cold Spring Harbor Laboratory Press). In a preferred method total RNA is isolated (Kamalay et al., (Cell (1980) 19:935–946) and polyadenylated mRNA is purified by standard means. mRNA is incorporated into a suitable phage such as lambda phage and used to transform a suitable host such as $E.$ $coli.$ Transformed clones are screened for positively hybridizing plaques using the radio-labelled, PCR derived probe.

In this manner DNA fragments were selected from both soybean and canola that had potential for encoding an acyl-ACP thioesterase. The DNA fragment isolated from soybean is identified as SEQ ID NO:1 and the DNA fragments isolated from canola are identified as SEQ ID NO:2 and SEQ ID NO:31.

Expression of Soybean and Canola Acyl-ACP Thioesterase Encoding DNA in E. coli In order to verify the function of the isolated soybean and canola DNA fragments it was necessary to express the fragments in recombinant hosts for protein purification and analysis of enzyme activity.

The present invention provides vectors and host cells suitable for genetic manipulations and the expression of recombinant proteins. Suitable hosts may include a variety of gram negative and gram positive bacteria where $E.$ $coli$ is generally preferred. Examples of bacteria-derived vectors include plasmid vectors such as pBR322, pUC19, pSP64, pUR278 and pORF1. Illustrative of suitable viral vectors are those derived from phage, vaccinia, and a variety of viruses. Examples of phage vectors include $1^+$, 1EMBL3, 12001, 1gt10, 1gt11, Charon 4a, Charon 40, and 1ZAP/R. pXB3 and pSC11 are exemplary of vaccinia vectors (Chakrabarti et al., *Molec. Cell. Biol.* 5:3401–9 (1985) and Mackett et al. *J. Virol.* 49:857864 (1984). Preferred in the present invention are the bacteria derived vectors such as pET-3d (described by F. W. Studier, A. H. Rosenberg, J. J. Dunn and J. W. Dubendorff, Methods in Enzymology Vol. 185) and the host $E.$ $coli$ strain BL21(DE3)(pLysE).

Once suitable vectors are constructed they are used to transform suitable bacterial hosts. Introduction of desired DNA fragments into $E.$ $coli$ may be accomplished by known procedures such as by transformation, e.g., using calcium-permeabilized cells, electroporation, or by transfection using a recombinant phage virus. (Sambrook et al., supra.)

For the expression of the soybean and canola DNA fragments (SEQ ID NO:1 and 2, respectively) the fragments were first cut with the appropriate restriction enzymes for the isolation of the region encoding the mature protein. Following this the restriction fragments were ligated to an appropriate linker sequence and inserted into a suitable vector downstream of an appropriate promoter. Suitable promoters may be either inducible or constitutive and are preferably derived from bacteria. Examples of suitable promoters are T7 and lac.

Thioesterase Assay:

Methods for the measurement of thioesterase activity are known in the art (see, for example, Smith et al., *Biochem, J.* 212, 155, (1983) and Spencer et al., *J. Biol. Chem.*, 253, 5922, (1978)). For the purpose of the present invention a modification of the method of Mckeon and Stumpf [J. Biol. Chem. (1982) 257:12141–12147] was used involving the synthesis of radiolabelled substrate ($[^{14}C]$acyl-ACP) using ACP and ACP synthetase isolated from $E.$ $coli.$ Solutions of $[^{14}C]$ palmitic acid, $[^{14}C]$ stearic acid, $[^{14}C]$ oleic acid, $[^{14}C]$ lauric acid, and $[^{14}C]$ decanoic acid were added to purified ACP in the presence of ACP synthetase and the resulting radiolabelled acyl ACP was purified by standard methods. Activity of the protein encoded and expressed by SEQ ID NO:1 and SEQ ID NO:2 was measured on the basis of the amount of $[^{14}C]$ substrate that was hydrolyzed.

Inhibition of Plant Target Genes by Use of Antisense RNA

Antisense RNA has been used to inhibit plant target genes in a tissue-specific manner (see van der Krol et al., Biotechniques (1988) 6:958–976). Antisense inhibition has been shown using the entire cDNA sequence (Sheehy et al., Proc. Natl. Acad. Sci. USA (1988) 85:8805–8809) as well as a partial cDNA sequence (Cannon et al., Plant Molec. Biol. (1990) 15:39–47). There is also evidence that the 3' non-coding sequences (Ch'ng et al., Proc. Natl. Acad. Sci. USA (1989) 86:10006–10010) and fragments of 5' coding sequence, containing as few as 41 base-pairs of a 1.87 kb cDNA (Cannon et al., Plant Molec. Biol. (1990) 15:39–47), can play important roles in anti-sense inhibition.

The entire soybean palmitoyl-ACP thioesterase cDNA was cloned in the anti-sense orientation with respect to a soybean β-conglycinin promoter and the chimeric gene transformed into soybean somatic embryos. As demonstrated in Example 2, these embryos serve as good model system for soybean zygotic embryos. Transformed somatic embryos showed inhibition of palmitate and possibly stearate biosyntheis. Similarly, the entire *Brassica napus* palmitoyl-ACP cDNA was cloned in the anti-sense orientation with respect to a rapeseed napin promoter and the chimeric gene transformed into *B. napus*.

Inhibition of Plant Target Genes by Cosuppression

The phenomenon of cosuppression has also been used to inhibit plant target genes in a tissue-specific manner. Cosuppression of an endogenous gene using the entire cDNA sequence (Napoli et al., The Plant Cell (1990) 2:279–289; van der Krol et al., The Plant Cell (1990) 2:291–299) as well as a partial cDNA sequence (730 bp of a 1770 bp cDNA) (Smith et al., Mol. Gen. Genetics (1990) 224:477–481) are known.

The nucleic acid fragments of the instant invention encoding palmitoyl-ACP thioesterases or parts thereof, with suitable regulatory sequences, can be used to reduce the level of palmitoyl-ACP thioesterase, thereby altering fatty acid composition, in transgenic plants which contain an endogenous gene substantially homologous to the introduced nucleic acid fragment. The experimental procedures necessary for this are similar to those described above for the anti-sense expression of palmitoyl-ACP thioesterase nucleic acid fragments except that one may use a either whole or partial cDNA.

Endogenous genes can also be inhibited by non-coding regions of an introduced copy of the gene [for example, Brusslan, J. A., et al. (1993) Plant Cell 5:667–677; Matzke, M. A. et al Plant Molecular Biology 16:821–830].

Selection of Hosts, Promoters and Enhancers

A preferred class of heterologous hosts for the expression of the nucleic acid fragments of the invention are eukaryotic hosts, particularly the cells of higher plants. Particularly preferred among the higher plants are the oil-producing species, such as soybean (Glycine max), rapeseed (including Brassica napus, B. campestris), sunflower (Helianthus annus), cotton (Gossypium hirsutum), corn (Zea mays), cocoa (Theobroma cacao), safflower (Carthamus tinctorius), oil palm (Elaeis guineensis), coconut palm (Cocos nucifera), flax (Linum usitatissimum), and peanut (Arachis hypogaea).

Expression in plants will use regulatory sequences functional in such plants. The expression of foreign genes in plants is well-established (De Blaere et al., Meth. Enzymol. (1987) 153:277–291). The source of the promoter chosen to drive the expression of the fragments of the invention is not critical provided it has sufficient transcriptional activity to accomplish the invention by increasing or decreasing, respectively, the level of translatable mRNA for the fatty acid desaturases in the desired host tissue. Preferred promoters include (a) strong constitutive plant promoters, such as those directing the 19S and 35S transcripts in cauliflower mosaic virus (Odell et al., Nature (1985) 313:810–812; Hull et al., Virology (1987) 86:482–493), (b) tissue- or developmentally-specific promoters, and (c) other transcriptional promoter systems engineered in plants, such as those using bacteriophage T7 RNA polymerase promoter sequences to express foreign genes. Examples of tissue-specific promoters are the light-inducible promoter of the small subunit of ribulose 1,5-bis-phosphate carboxylase (if expression is desired in photosynthetic tissues), the maize zein protein promoter (Matzke et al., EMBO J. (1984) 3:1525–1532), and the chlorophyll a/b binding protein promoter (Lampa et al., Nature (1986) 316:750–752).

Particularly preferred promoters are those that allow seed-specific expression. This may be especially useful since seeds are the primary source of vegetable oils and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., Ann. Rev. Plant Physiol. (1984) 35:191–221; Goldberg et al., Cell (1989) 56:149–160). Moreover, different seed storage proteins may be expressed at different stages of seed development.

Expression of seed-specific genes has been studied in great detail (see reviews by Goldberg et al., Cell (1989) 56:149–160 and Higgins et al., Ann. Rev. Plant Physiol. (1984) 35:191–221). There are currently numerous examples of seed-specific expression of seed storage protein genes in transgenic dicotyledonous plants. These include genes from dicotyledonous plants for bean b-phaseolin (Sengupta-Gopalan et al., Proc. Natl. Acad. Sci. USA (1985) 82:3320–3324; Hoffman et al., Plant Mol. Biol. (1988) 11:717–729), bean lectin (Voelker et al., EMBO J. (1987) 6:3571–3577), soybean lectin (Okamuro et al., Proc. Natl. Acad. Sci. USA (1986) 83:8240–8244), soybean Kunitz trypsin inhibitor (Perez-Grau et al., Plant Cell (1989) 1:095–1109), soybean b-conglycinin (Beachy et al., EMBO J. (1985) 4:3047–3053; pea vicilin (Higgins et al., Plant Mol. Biol. (1988) 11:683–695), pea convicilin (Newbigin et al., Planta (1990) 180:461–470), pea legumin (Shirsat et al., Mol. Gen. Genetics (1989) 215:326–331); rapeseed napin (Radke et al., Theor. Appl. Genet. (1988) 75:685–694) as well as genes from monocotyledonous plants such as for maize 15 kD zein (Hoffman et al., EMBO J. (1987) 6:3213–3221), maize 18 kD oleosin (Lee et al., Proc. Natl. Acad. Sci. USA (1991) 888:6181–6185), barley b-hordein (Marris et al., Plant Mol. Biol. (1988) 10:359–366) and wheat glutenin (Colot et al., EMBO J. (1987) 6:3559–3564). Moreover, promoters of seed-specific genes operably linked to heterologous coding sequences in chimeric gene constructs also maintain their temporal and spatial expression pattern in transgenic plants. Such examples include use of Arabidopsis thaliana 2S seed storage protein gene promoter to express enkephalin peptides in Arabidopsis and B. napus seeds (Vandekerckhove et al., Bio/Technology (1989) 7:929–932), bean lectin and bean b-phaseolin promoters to express luciferase (Riggs et al., Plant Sci. (1989) 63:47–57), and wheat glutenin promoters to express chloramphenicol acetyl transferase (Colot et al., EMBO J. (1987) 6:3559–3564).

Of particular use in the expression of the nucleic acid fragment of the invention will be the heterologous promoters from several soybean seed storage protein genes such as those for the Kunitz trypsin inhibitor (Jofuku et al., Plant Cell (1989) 1:1079–1093; glycinin (Nielson et al., Plant Cell (1989) 1:313–328), and b-conglycinin (Harada et al., Plant Cell (1989) 1:415–425). Promoters of genes for a- and b-subunits of soybean b-conglycinin storage protein will be particularly useful in expressing the mRNA or the antisense RNA in the cotyledons at mid- to late-stages of seed development (Beachy et al., EMBO J. (1985) 4:3047–3053) in transgenic plants. This is because there is very little position effect on their expression in transgenic seeds, and the two promoters show different temporal regulation. The promoter for the a-subunit gene is expressed a few days before that for the b-subunit gene. This is important for transforming rapeseed where oil biosynthesis begins about a week before seed storage protein synthesis (Murphy et al., J. Plant Physiol. (1989) 135:63–69).

Also of particular use will be promoters of genes expressed during early embryogenesis and oil biosynthesis. The native regulatory sequences, including the native promoters, of the palmitoyl-ACP thioesterase genes expressing the nucleic acid fragments of the invention can be used following their isolation by those skilled in the art. Heterologous promoters from other genes involved in seed oil biosynthesis, such as those for B. napus isocitrate lyase and malate synthase (Comai et al., Plant Cell (1989) 1:293–300), delta-9 desaturase from safflower (Thompson et al. Proc. Natl. Acad. Sci. USA (1991) 88:2578–2582) and castor (Shanklin et al., Proc. Natl. Acad. Sci. USA (1991) 88:2510–2514), acyl carrier protein (ACP) from Arabidopsis (Post-Beittenmiller et al., Nucl. Acids Res. (1989) 17:1777), B. napus (Safford et al., Eur. J. Biochem. (1988) 174:287–295), and B. campestris (Rose et al., Nucl. Acids Res. (1987) 15:7197), b-ketoacyl-ACP synthetase from barley (Siggaard-Andersen et al., Proc. Natl. Acad. Sci. USA (1991) 88:4114–4118), and oleosin from Zea mays (Lee et al., Proc. Natl. Acad. Sci. USA (1991) 88:6181–6185), soybean (Genbank Accession No: X60773) and *B. napus* (Lee et al., Plant Physiol. (1991) 96:1395–1397) will be of use. If the sequence of the corresponding genes is not disclosed or their promoter region is not identified, one skilled in the art can use the published sequence to isolate the corresponding gene and a fragment thereof containing the promoter. The partial protein sequences for the relatively-abundant enoyl-ACP reductase and acetyl-CoA carboxylase are also published (Slabas et al., Biochim. Biophys. Acta (1987) 877:271–280; Cottingham et al., Biochim. Biophys. Acta (1988) 954:201–207) and one skilled in the art can use these sequences to isolate the corresponding seed genes with their promoters. Attaining the proper level of expression of the nucleic acid fragments of the invention may require the use of different chimeric genes utilizing different promoters. Such chimeric genes can be transferred into host plants either together in a single expression vector or sequentially using more than one vector.

It is envisioned that the introduction of enhancers or enhancer-like elements into the promoter regions of either the native or chimeric nucleic acid fragments of the invention will result in increased expression to accomplish the invention. This would include viral enhancers such as that found in the 35S promoter (Odell et al., Plant Mol. Biol. (1988) 10:263–272), enhancers from the opine genes (Fromm et al., Plant Cell (1989) 1:977–984), or enhancers from any other source that result in increased transcription when placed into a promoter operably linked to the nucleic acid fragment of the invention.

Of particular importance is the DNA sequence element isolated from the gene for the a-subunit of b-conglycinin that can confer 40-fold seed-specific enhancement to a constitutive promoter (Chen et al., Dev. Genet. (1989) 10:112–122). One skilled in the art can readily isolate this element and insert it within the promoter region of any gene in order to obtain seed-specific enhanced expression with the promoter in transgenic plants. Insertion of such an element in any seed-specific gene that is expressed at different times than the b-conglycinin gene will result in expression in transgenic plants for a longer period during seed development.

Any 3' non-coding region capable of providing a polyadenylation signal and other regulatory sequences that may be required for the proper expression of the nucleic acid fragments of the invention can be used to accomplish the invention. This would include 3' ends of the native fatty acid desaturase(s), viral genes such as from the 35S or the 19S cauliflower mosaic virus transcripts, from the opine synthesis genes, ribulose 1,5-bisphosphate carboxylase, or chlorophyll a/b binding protein. There are numerous examples in the art that teach the usefulness of different 3' non-coding regions.

Transformation Methods

Various methods of transforming cells of higher plants according to the present invention are available to those skilled in the art (see EPO Pub. 0 295 959 A2 and 0 318 341 A1). Such methods include those based on transformation vectors utilizing the Ti and Ri plasmids of Agrobacterium spp. It is particularly preferred to use the binary type of these vectors. Ti-derived vectors transform a wide variety of higher plants, including monocotyledonous and dicotyledonous plants (Sukhapinda et al., Plant Mol. Biol. (1987) 8:209–216; Potrykus, Mol. Gen. Genet. (1985) 199:183). Other transformation methods are available to those skilled in the art, such as direct uptake of foreign DNA constructs (see EPO Pub. 0 295 959 A2), techniques of electroporation (Fromm et al., Nature (1986) (London) 319:791) or high-velocity ballistic bombardment with metal particles coated with the nucleic acid constructs (Kline et al., Nature (1987) (London) 327:70). Once transformed, the cells can be regenerated by those skilled in the art.

Of particular relevance are the recently described methods to transform foreign genes into commercially important crops, such as rapeseed (De Block et al., Plant Physiol. (1989) 91:694–701), sunflower (Everett et al., Bio/Technology (1987) 5:1201), and soybean (Christou et al., Proc. Natl. Acad. Sci USA (1989) 86:7500–7504.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

MATERIALS AND METHODS

Various solutions used in the experimental manipulations are referred to by their common names such as "SSC", "SSPE", "Denhardt's solution", etc. The composition of these solutions as well as any method for the standard manipulation of nucleic acids, transformatins and growth of *E. coli* may be found by reference to Sambrook, et al. (Molecular Cloning, A Laboratory Manual, 2nd ed. (1989), Cold Spring Harbor Laboratory Press)

Growth Media:

Media for the growth of plant embryo cultures is given below:

| Plant Embryo Culture Media | |
|---|---|
| Media: | |
| SB55 and SBP6 Stock Solutions (g/L): | |
| MS Sulfate 100X Stock | |
| $MgSO_4$ $7H_2O$ | 37.0 |
| $MnSO_4$ $H_2O$ | 1.69 |
| $ZnSO_4$ $7H_2O$ | 0.86 |
| $CuSO_4$ $5H_2O$ | 0.0025 |
| MS Halides 100X Stock | |
| $CaCl_2$ $2H_2O$ | 44.0 |
| KI | 0.083 |
| $CoCl_2$ $6H_2O$ | 0.00125 |
| $KH_2PO_4$ | 17.0 |
| $H_3BO_3$ | 0.62 |
| $Na_2MoO_4$ $2H_2O$ | 0.025 |
| MS FeEDTA 100X Stock | |
| $Na_2EDTA$ | 3.724 |
| $FeSO_4$ $7H_2O$ | 2.784 |
| B5 Vitamin Stock | |
| 10 g m-inositol | |
| 100 mg nicotinic acid | |
| 100 mg pyridoxine HCl | |
| 1 g thiamine | |
| SB55 (per Liter) | |
| 10 mL each MS stocks | |

-continued

Plant Embryo Culture Media 1 mL B5 Vitamin stock
0.8 g NH$_4$NO$_3$
3.033 g KNO$_3$
1 mL 2,4-D (10 mg/mL stock)
60 g sucrose
0.667 g asparagine
pH 5.7
For SBP6- substitute 0.5 mL 2,4-D
SB103 (per Liter)

MS Salts
6% maltose
750 mg MgCl$_2$
0.2% Gelrite
pH 5.7
SB71-1 (per liter)

B5 salts
1 mL B5 vitamin stock
3% sucrose
750 mg MgCl$_2$
0.2% gelrite
pH 5.7

Media for the transformation of *Brassica Napus* cells and the growth of agrobacterium described in Example 4 is as follows:

Minimal A Bacterial Growth Medium

Dissolve in distilled water:
  10.5 grams potassium phosphate, dibasic
  4.5 grams potassium phosphate, monobasic
  1.0 gram ammonium sulfate
  0.5 gram sodium citrate, dihydrate
  Make up to 979 mL with distilled water
  Autoclave
  Add 20 mL filter-sterilized 10% sucrose
  Add 1 mL filter-sterilized 1 M MgSO$_4$

*Brassica Callus* Medium BC-28

Per liter:
  Murashige and Skoog Minimal Organic Medium (MS salts, 100 mg/L i-inositol, 0.4 mg/L thiamine; GIBCO #510-3118)
  30 grams sucrose
  18 grams mannitol
  1.0 mg/L 2,4-D
  0.3 mg/L kinetin
  0.6% agarose
  pH 5.8

Brassica Regeneration Medium BS-48

Murashige and Skoog Minimal Organic Medium
Gamborg B5 Vitamins (SIGMA #1019)
10 grams glucose
250 mg xylose
600 mg MES
0.4% agarose
pH 5.7
Filter-sterilize and add after autoclaving:
  2.0 mg/L zeatin
  0.1 mg/L IAA

Brassica Shoot Elongation Medium MSV-1A

Murashige and Skoog Minimal Organic Medium
Gamborg B5 Vitamins
10 grams sucrose
0.6% agarose
pH 5.8

Thioesterase assay:

To assay for the presence of thioesterase activity [$^{14}$C] radiolabled acyl ACP substrates were prepared. Preparation of the substrates required the isolation of ACP and ACP synthetase from *E. coli* and the enzymatic reaction of [$^{14}$C] fatty acid with the ACP protein.

Purification of Acyl Carrier Protein (ACP) from *E. coli*

To frozen *E. coli* cell paste, (0.5 kg of 1/2 log phase growth of *E. coli* B grown on minimal media and obtained from Grain Processing Corp, Muscatine, Iowa.) was added 50 mL of a solution 1M in Tris, 1M in glycine, and 0.25 M in EDTA. Ten mL of 1M MgCl$_2$ was added and the suspension was thawed in a water bath at 50° C. As the suspension approached 37° C. it was transferred to a 37° C. bath, made to 10 mM in 2-mercaptoethanol and 20 mg of DNAse and 50 mg of lysozyme were added. The suspension was stirred for 2 h, then sheared by three 20 second bursts in a Waring Blendor. The volume was adjusted to 1 L and the mixture was centrifuged at 24,000×g for 30 min. The resultant supernatant was centrifuged at 90,000×g for 2 h. The resultant high-speed pellet was saved for extraction of acyl-ACP synthase (see below) and the supernatant was adjusted to pH 6.1 by the addition of acetic acid. The extract was then made to 50% in 2-propanol by the slow addition of cold 2-propanol to the stirred solution at 0° C. The resulting precipitate was allowed to settle for 2 h and then removed by centrifugation at 16,000×g. The resultant supernatant was adjusted to pH 6.8 with KOH and applied at 2 mL/min to a 4.4×12 cm column of DEAE-Sephacel which had been equilibrated in 10 mM MES, pH 6.8. The column was washed with 10 mM MES, pH 6.8 and eluted with 1 L of a gradient of LiCl from 0 to 1.7M in the same buffer. Twenty mL fractions were collected and the location of eluted ACP was determined by applying 10 μL of every second fraction to a lane of a native polyacrylamide (20% acrylamide) gel electrophoresis (PAGE). Fractions eluting at about 0.7M LiCl contained nearly pure ACP and were combined, dialyzed overnight against water and then lyophilized.

Purification of Acyl-ACP Synthase

Membrane pellets resulting from the high-speed centrifugation described above were homogenized in 380 mL of 50 mM Tris-Cl, pH 8.0, and 0.5 M in NaCl and then centrifuged at 80,000×g for 90 min. The resultant supernatant was discarded and the pellets resuspended in 50 mM Tris-Cl, pH 8.0, to a protein concentration of 12 mg/mL. The membrane suspension was made to 2% in Triton X-100 and 10 mM in MgCl$_2$, and stirred at 0° C. for 20 min before centrifugation at 80,000×g for 90 min. The protein in the resultant supernatant was diluted to 5 mg/mL with 2% Triton X-100 in 50 mM Tris-Cl, pH 8.0 and, then, made to 5 mM ATP by the addition of solid ATP (disodium salt) along with an equimolar amount of NaHCO$_3$. The solution was warmed in a 55° C. bath until the internal temperature reached 53° C. and was then maintained at between 53° C. and 55° C. for 5 min. After 5 min the solution was rapidly cooled on ice and centrifuged at 15,000×g for 15 min. The supernatant from the heat treatment step was loaded directly onto a column of 7 mL Blue Sepharose 4B which had been equilibrated in 50 mM Tris-Cl, pH 8.0, and 2% Triton X-100. The column was washed with 5 volumes of the loading buffer, then 5 volumes of 0.6 M NaCl in the same buffer and the activity was eluted with 0.5 M KSCN in the same buffer. Active fractions were assayed for the synthesis of acyl-ACP, as described below, combined, and bound to 3 mL settled-volume of hydroxlyapatite equilibrated in 50 mM Tris-Cl, pH 8.0, 2% Triton X-100. The hydroxylapatite was collected by centrifugation, washed twice with 20 mL of 50 mM Tris-Cl, pH 8.0, 2% Triton X-100. The activity was eluted with two 5 mL washes of 0.5 M potassium phosphate, pH 7.5, 2% Triton X-100. The first wash contained 66% of the activity and it was concentrated with a 30 kD membrane filtration concentrator (Amicon) to 1.5 mL.

Synthesis of Radiolabeled Acyl-ACP

A solutions of [$^{14}$C] palmitic acid, [$^{14}$C] stearic acid, [$^{14}$C] oleic acid, [$^{14}$C] lauric acid, and [$^{14}$C] decanoic acid (120 nmoles each) prepared in methanol were dried in glass reaction vials. The ACP preparation described above (1.15 mL, 32 nmoles) was added along with 0.1 mL of 0.1 M ATP, 0.05 mL of 80 mM DTT, 0.1 mL of 8 M LiCl, and 0.2 mL of 13% Triton X-100 in 0.5 M Tris-Cl, pH 8.0, with 0.1 M MgCl$_2$. The reaction was mixed thoroughly and 0.3 mL of the acyl-ACP synthase preparation was added and the reaction was incubated at 37° C. After one-half h intervals a 10 μL aliquot was taken and dried on a small filter paper disc. The disc was washed extensively with chloroform:methanol:acetic acid (8:2:1, v:v:v) and radioactivity retained on the disc was taken as a measure of [$^{14}$C]- acyl-ACP. At 2 h about 88% of the ACP had been consumed. The reaction mixes were diluted 1 to 4 with 20 mM Tris-Cl, pH 8.0, and applied to 1 mL DEAE-Sephacel columns equilibrated in the same buffer. The columns were washed in sequence with 5 mL of 20 mM Tris-Cl, pH 8.0, 5 mL of 80% 2-propanol in 20 mM Tris-Cl, pH 8.0, and eluted with 0.5 M LiCl in 20 mM Tris-Cl, pH 8.0. The column eluates were passed directly onto 3 mL columns of octyl-sepharose CL-4B which were washed with 10 mL of 20 mM potassium phosphate, pH 6.8, and then eluted with 35% 2-propanol in 2 mM potassium phosphate, pH 6.8. The eluted products were lyophilized and redissolved at a concentration of 24 μM.

Example 1

ISOLATION OF CDNA'S FOR SOYBEAN AND CANOLA SEED PALMITOYL-ACP THIOESTERASE

PCR Synthesis of a DNA Probe for an Arabidopsis cDNA with Sequence Homology to a Medium Chain Fatty acyl-ACP Thioesterase A portion of the sequence of an Arabidopsis cDNA sequenced in the *Arabidopsis thaliana* transcribed genome sequencing project (clone YAP140T7) obtained from Genbank entry Z17678 (*Arabidopsis thaliana* systematic cDNA sequencing reveals a gene with homology with *Umbellularia californica* C12:0-ACP thioesterase. (Francoise et al., Plant Physiol. Biochem. 31, 599, (1993)) and additional sequence from an *Arabidopsis thaliana* cDNA clone obtained using that sequence and communicated by Dr. John Ohrolgge (Michigan State University) were used to make two PCR primers shown in SEQ ID NO:3 (the 5' extending primer) and SEQ ID NO:4 (the 3' extending primer). Total RNA was extracted from green seliques of Arabidopis plants and polysomal RNA was isolated following the procedure of Kamalay et al., (Cell (1980) 19:935–946). The polyadenylated mRNA fraction was obtained by affinity chromatography on oligo-dT cellulose (Aviv et al., Proc. Natl. Acad. Sci. USA (1972) 69:1408–1411). Thirteen ng of the polyadenylated mRNA was used as template for amplification from oligo-dT using a GeneAmp® RNA-PCR kit (Perkin Elmer Cetus, part number N808-0017). PCR was done at an annealing temperature of 52° C. for 35 cycles. A DNA fragment of about 560 base pairs was generated and isolated by agarose gel purification.

The isolated fragment was used as the template for random primer labeling with [$^{32}$P]dCTP.

Cloning of a *Brassica napus* Seed cDNA Homologus to the Arabidopis Thioesterase Like Fragment The radiolabelled probe was used to screen a *Brassica napus* seed cDNA library. In order to construct the library, *Brassica napus* seeds were harvested 20–21 days after pollination, placed in liquid nitrogen, and polysomal RNA was isolated following the procedure of Kamalay et al., (Cell (1980) 19:935–946). The polyadenylated mRNA fraction was obtained by affinity chromatography on oligo-dT cellulose (Aviv et al., supra). Four micrograms of this mRNA were used to construct a seed cDNA library in lambda phage (Uni-ZAP__ XR vector) using the protocol described in the ZAP-cDNA__ Synthesis Kit (1991 Stratagene Catalog, Item #200400). Approximately 240,000 clones were screened for positively hybridizing plaques using the radiolabelled, PCR derived probe described above essentially as described in Sambrook et al., supra except that low stringency hybridization conditions (50 mM Tris, pH 7.6, 6×SSC, 5×Denhardt's, 0.5% SDS, 100 μg denatured calf thymus DNA and 50° C.) were used and post-hybridization washes were performed twice with 2×SSC, 0.5% SDS at room temperature for 15 min, then twice with 0.2×SSC, 0.5% SDS at room temperature for 15 min, and then twice with 0.2×SSC, 0.5% SDS at 50° C. for 15 min. Nine positive plaques showing strong hybridization were picked, plated out, and the screening procedure was repeated. From the secondary screen four, pure phage plagues were isolated. Plasmid clones containing the cDNA inserts were obtained through the use of a helper phage according to the in vivo excision protocol provided by Stratagene. Double-stranded DNA was prepared using the Magic® Miniprep (Promega) and the manufacturers instructions, and the resulting plasmids were size-analyzed by electrophoresis in agarose gels. One of the four clones, designated p5a, contained an approximately 1.5 kb insert which was sequenced from both strands by the di-deoxy method. The sequence of 1483 bases of the cDNA insert of p5a is shown in SEQ ID NO:2. A second clone, designated p2a was also sequenced and found to contain a 1673 base pair cDNA shown in SEQ ID NO:31. The sequences of the two cDNA inserts are 85% identical overall, they encode peptides that are 92% identical overall but which are 94% identical within the region of the putative mature peptide (the peptide after removal of the plastid transit sequence). The cDNA regions of the two cDNAs which encode the mature peptides are 90.4% identical. The two cDNAs probably encode two isozymes of the same activity. Based on the length of the transit peptides for the two sequences, the length of the respective cDNAs and alignments to the soybean sequences shown below, it appears that the cDNA in clone p5a is a slightly truncated version of the actual message while clone p2a represents a full length message. The cDNA isolated from clone p2a has been sequenced and the sequence is given in SEQ ID NO 31. Cloning of a Soybean Seed cDNA Homologus to the Arabidopis Thioesterase Like Fragment A cDNA library was made as follows: Soybean embryos (ca. 50 mg fresh weight each) were removed from the pods and frozen in liquid nitrogen. The frozen embryos were ground to a fine powder in the presence of liquid nitrogen and then extracted by Polytron homogenization and fractionated to enrich for total RNA by the method of Chirgwin et al. (Biochemistry (1979) 18:5294–5299). The nucleic acid fraction was enriched for poly A$^+$RNA by passing total RNA through an oligo-dT cellulose column and eluting the poly A$^+$RNA with salt as described by Goodman et al. (Meth. Enzymol. (1979) 68:75–90). cDNA was synthesized from the purified poly A$^+$RNA using cDNA Synthesis System (Bethesda Research Laboratory) and the manufacturer's instructions. The resultant double-stranded DNA was methylated by Eco RI DNA methylase (Promega) prior to filling-in its ends with T4 DNA polymerase (Bethesda Research Laboratory) and blunt-end ligation to phosphorylated Eco RI linkers using T4 DNA ligase (Pharmacia, Upsalla Sweden). The double-stranded DNA was digested with Eco RI enzyme, separated from excess linkers by passage through a gel filtration column (Sepharose CL-4B), and ligated to lambda ZAP vector (Stratagene, 1109 N. Torrey Pine Rd., LaJolla Calif.) according to manufacturer's instructions. Ligated DNA was packaged into phage using the Gigapack packaging extract (Stratagene) according to manufacturer's instructions. The resultant cDNA library was amplified as per Stratagene's instructions and stored at −80° C.

Following the instructions in the Lambda ZAP Cloning Kit Manual (Stratagene), the cDNA phage library was used to infect *E. coli* BB4 cells and a total of approximately 360,000 plaque forming units were plated onto 6, 150 mm diameter petri plates. Duplicate lifts of the plates were made onto nitrocellulose filters (Schleicher & Schuell). The filters were prehybridized in 25 mL of hybridization buffer consisting of 6×SSPE, 5×Denhardt's solution, 0.5% SDS, 5% dextran sulfate and 0.1 mg/mL denatured salmon sperm DNA (Sigma Chemical Co.) at 50° C. for 2 h. Radiolabelled probe based on the Arabidopsis PCR product described above was added, and allowed to hybridize for 18 h at 50° C. The filters were washed exactly as described above. Autoradiography of the filters indicated that there were 9 strongly hybridizing plaques. The 9 plaques were subjected to a second round of screening as before.

From the secondary screen three, pure phage plaques were isolated. Plasmid clones containing the cDNA inserts were obtained through the use of a helper phage according to the in vivo excision protocol provided by Stratagene. Double-stranded DNA was prepared using the Magic® Miniprep (Promega) and the manufacturers instructions, and the resulting plasmids were size-analyzed by electrophoresis in agarose gels. One of the four clones, designated p233b, contained an approximately 1.2 kb insert one strand of which was partially sequenced by the di-deoxy method. The 311 bases of p233b that were sequenced showed a sequence identity of 81.2% in comparison to the Arabidopsis thioesterase like sequence which was the basis for the PCR probe. The other two clones isolated from the inital screening appeared to be cDNA concatomers in which the primary inserts were of a size similar to p233a. Comparison of the sequence at the 5 prime end of p233a to both the canola sequence and the Arabidopsis sequence indicated that p233a is a 5 prime truncated version of the putative thioesterase. The cDNA insert of p233b was removed by digestion with Eco RI and the insert was purified by agarose gel electrophoresis. The purified insert was used as the template for random primer labeling as described above. Approximately 150,000 plaque forming units of the soybean seed cDNA library were plated on three plates as described above and duplicate nitrocellulose lifts were screened at high stringency (hybridization at 60° C. in 6×SCC, 0.1% SDS for 18 hr, washing at 60° C. in 0.2×SSC, 0.1% SDS twice for 10 min each). Of 18 positive plaques obtained, one designated pTE11, and containing a 1.5 kB insert was chosen for sequencing by the di-deoxy method. The sequence of the 1688 bases in the soybean cDNA insert of pTE11 are shown in SEQ ID 1.

Example 2

EXPRESSION OF THE CATALYTICALLY ACTIVE PROTEIN ENCODED BY THE SOYBEAN AND CANOLA cDNA'S HOMOLOGUS TO THE PUTATIVE THIOESTERASE FROM ARABIDOPSIS IN *E. COLI*

Plasmid vectors for the expression of the portions of the soybean and canola putative thioesterase cDNA's assumed to encode the pro-protein were made using the vector pET-3d (described by F. W. Studier, A. H. Rosenberg, J. J. Dunn and J. W. Dubendorff, Methods in Enzymology Vol. 185) and the host cell strain BL21(DE3)(pLysE).

The canola clone p5a was digested with Pvu II and Hin DIII to release a 1235 base pair fragment which was blunted with DNA polymerase I before isolation by agarose gel electrophoresis. Two oligonucletides were synthesisized which, when annealed together form the following linker sequence:
5'-CATGGAGGAGCAG (SEQ ID NO:3)
3'-CTCCTCGTC (SEQ ID NO:4)
The linkers were ligated to the 1235 base pair fragment which was then ligated into the Nco I digested and calf intestinal phosphatase treated pET-3d. The ligation mixture was used to transform competent BL21(DE3)(pLyE) cells and twenty ampicillin resistant clonies were used to innocculate 5 mL liquid cultures. Plasmid DNA was prepared from the cultures and digested with Pvu II, Nco I and Eco RI to determine the presence of an insert and its orientation with respect to the T7 promoter. Only one insert containing plasmid was obtained, and the orientation of the conding region with respect to the promoter was reversed. The plasmid DNA was digested with Nco I, the insert isolated and religated into Nco I digested, phosphatase treated pET-3d as above. The ligation mixture was used to transform competent XL-1 cells. Ten isolated colonies were used to inocculate 5 mL liquid cultures and plasmid DNA was isolated. Three clones were determined to be in the forward direction by their Eco RI restriction fragment pattern. The region across the cloning site was sequenced and found to place the start methionine encoded by the linker DNA sequence in frame with the protein encoded by the canola cDNA to give the deduce amino acid sequence shown in SEQ ID NO:6.

The soybean cDNA containing plamid pTE11 was digested with Sph I and Eco RI, blunted with DNA polymerase I and the resulting 1208 base pair fragment was isolated by agarose gel electrophoresis. The above described linkers were ligated to the fragment and the product was ligated into the pET-3b vector as described for the canola cDNA fragment above. The ligation mixture was used to transform competent XL-1 cells and ten of the colonies obtained were used to inocculate 5 mL liquid cultures. Plasmid DNA isolated from the cultures was digested with Nco I to determine the presence of a cDNA insert and with Hpa I and Sph I to determine the orientation of the insert relative to the T7 promoter. One clone with a correctly oriented insert was obtained and used to transform competent BL21(DE3)(pLysE) cells. The deduced amino acid sequence of the expressed protein is shown in SEQ ID NO:7.

Single colonies of the BL21(DE3)(pLysE) strains containing the pET: canola and the soybean cDNA expression vectors were used to inocculate 5 mL of 2×YT media containing 50 mg/L ampicillin. The cultures were grown overnight at 37° C., diluted to 0.1 OD at 600 nm with fresh, ampicillin containing media and re-grown to 1.5 OD at 600 nm at 37° C. Both cultures were induced by the addition of IPTG to a final concentration of 1 mM. Cells were harvested by centrifugation three hr after induction. A volume of lysis buffer (50 mM HEPES, pH 7.5, 15 mM NaCl, 0.5 mM EDTA, 1 mM DTT and 15% glycerol) approximately equal to the pellet volume was added and the cells were resuspended by vortex mixing. A small amount of 2 mm glass beads and 0.2 M PMSF in 2-propanol to a final concentration of 0.2 mM was added just before sonication. The cell lysate was centrifuged in a microfuge to clear and the supernatent of the canola cDNA expressing cell line was diluted one to twenty with 50 mM Tricine (pH 8.2, 1 mg/mL BSA and 1 mM DTT) to give a lysate protein concentration of 1.8 mg/mL. The cell line expressing the soybean cDNA was similarly diluted one to five to give a lysate protein concentration of 2.4 mg/mL.

Acyl-ACP Thioesterase Assay

Reagents and substrates for the thioesterase assay are prepared as described above in the the MATERIALS AND METHODS section. Acyl-ACP thioesterase was assayed as described by Mckeon and Stumpf [J. Biol. Chem. (1982) 257:12141–121471]. Each of the radiolabeled acyl-ACP's were adjusted to concentrations ranging from 0.18 µM to 2.06 µM and a volume of 40 µL with a reaction buffer consisting of 1 mg/mL bovine serum albumin in CAPS-NaOH buffer (50 mM) at pH 9.5. Reactions were started with lysate from E. coli expressing the plant cDNA's for the putative acyl-ACP thioesterase from either soybean seed or canola seed and incubated for times varying from 12 seconds to 1 min depending upon the activity of the fraction. Reactions were terminated by the addition of 100 µl of a solution of 5% acetic acid in 2-propanol and extracted twice with 1 mL each of water saturated hexane. Five mL of ScintiVerse Bio HP (Fisher) scintillation fluid was added to the combined extracts and radioactivity in the released fatty acids was determined by scintilation counting.

Thioesterase assays done on E. coli extracts from cultures which were not transformed with thioesterase expressing plasmids had specific activities of about 0.025 nmole/min/mg protein in the palmitoyl-ACP, stearoyl-ACP and oleoyl-ACP assays when the assay was done at 1 µM substrate concentration. Since this E. coli background was from 70 to 150 fold less than the activity found in the plant thioesterase expressing lines, it is ignored in the following data.

Assays were done at 4 substrate concentrations for the soybean enzyme and at a concentration which gave maximal activity for the canola enzyme. Assays were done such that less than 25% of the available substrate was consumed at each substrate concentration and the substrate concentration listed in Table 2 is the average concentration during the time of the reaction.

TABLE 2

Activity of the Soybean and Canola Thioesterases Against Palmitoly-ACP, Stearoyl-ACP and Oleoyl-ACP

| SUBSTRATE | SPECIFIC ACTIVITY (nmole/min/mg protein) |
|---|---|
| Soybean Thioesterase | |
| Palmitoyl-ACP | |
| 0.18 µM | 1.17 |
| 0.37 µM | 1.87 |
| 0.74 µM | 3.43 |
| 1.01 µM | 3.61 |
| Stearoyl-ACP | |
| 0.18 µM | 0.67 |
| 0.41 µM | 1.08 |
| 0.81 µM | 1.80 |
| 1.62 µM | 1.76 |
| Oleoyl-ACP | |
| 0.18 µM | 0.21 |
| 0.41 µM | 0.77 |
| 1.03 µM | 0.86 |
| 2.06 µM | 0.98 |
| Palmitoyl-ACP* | |
| 0.58 µM | 17.6 |
| Docecanoly-ACP* | |
| 0.54 µM | 0.11 |
| Lauroyl-ACP* | |
| 0.54 µM | 0.07 |
| Canola Thioesterase | |
| Palmitoyl-ACP | |
| 1.01 µM | 3.33 |
| Stearoyl-ACP | |
| 0.81 µM | 1.27 |
| Oleoyl-ACP | |
| 1.03 µM | 1.76 |

*Data from a seperate experiment in which the pET:soybean palmitolyl thioesterase was expressed to a higher level in BL21 (DE3) cells.

The data in Table 2 shows that both the canola and the soybean enzymes are acyl-ACP thioesterases. While neither enzyme has significant activity toward lauroyl-ACP or decanoly-ACP which is the substrate for the enzyme that they were initially idenified as homologus to (Arabidopsis thaliana systematic cDNA sequencing reveals a gene with homology with Umbellularia californica C12:0-ACP thioesterase. Francoise Grellet, Richard Cooke, Monique Raynal, Michele Laudie and Michel Delseny, Plant Physiol. Biochem. 1993 31:599–602), both are active against longer acyl chain-ACP's. Both have a preference of between two and three fold for palmitoyl-ACP over either stearoyl-ACP or oleoyl-ACP. This is in contrast to the known acyl-ACP thioesterases from these species which show a strong substrate preference for oleoyl-ACP [WO 9211373]. The enzymes thus represent a second class of acyl-ACP thioesterase, present within the same tissues as the oleoyl-ACP thioesterase which have substrate preference for long chain, saturated acyl-ACP's.

Example 3

REGULATION OF THE EXPRESSION OF PALMITOYL-ACP THIOESTERASE IN SOYBEANS

Construction of Vectors for Transformation of Glycine max for Reduced Expression of Palmitoyl-ACP thioesterase in Developing Soybean Seeds Plasmids containing the antisense *G. max* palmitoyl-ACP thioesterase cDNA sequence under control of the soybean beta-conglycinin promoter (Beachy et al., EMBO J. (1985) 4:3047–3053), were constructed. The construction of vectors expressing the soybean delta-12 desaturase antisense cDNA under the control of these promoters was facilitated by the use of plasmids pCW109 and pML18, both of which are described in [WO 9411516].

A unique Not I site was introduced into the cloning region between the beta-conglicinin promoter and the phaseolin 3' end in pCW109 by digestion with Nco I and Xba I followed by removal of the single stranded DNA ends with mung bean exonuclease. Not I linkers (New England Biochemical catalog number NEB 1125) were ligated into the linearized plasmid to produce plasmid pAW35. The single Not I site in pML18 was destroyed by digestion with Not I, filling in the single stranded ends with dNTP's and Klenow fragment followed by re-ligation of the linearized plasmid. The modified pML18 was then digested with Hind III and treated with calf intestinal phosphatase.

The beta-conglicinin:Not I:phaseolin expression cassette in pAW35 was removed by digestion with Hind III and the 1.79 kB fragment was isolated by agarose gel electrophoresis. The isolated fragment was ligated into the modified and linearized pML18 construction described above. A clone with the desired orientation was identified by digestion with Not I and Xba I to release a 1.08 kB fragment indicating that the orientation of the beta-conglycinin transcription unit was the same as the selectable marker transcription unit. The resulting plasmid was given the name pBS19.

PCR amplification primers SOYTE3 (5'-AAGGAAAAAAGCGGCCGCTGACACAATAGCCCTTCT-3') (SEQ ID NO:5) corresponding to bases 1 to 16 of SEQ ID NO:1 with additional bases to provide a Not I restriction site and sufficient additional bases to allow Not I digestion and SOYTE4 (5-AAGGAAAAAAGCGGCCGCGATTTACTGCTGCTTTTC-3') (SEQ ID NO:12) corresponding to the reverse complement of bases 1640 to 1657 of SEQ ID NO:1 with additional bases to provide a Not I restriction site and sufficient additional bases to allow Not I digestion were synthesiszed. Using these primers, pTE11 as template and standard PCR amplification proccedures (Perkin Elmer Cetus, GeneAmp PCR kit), a 1.6 kB fragment of p233b was amplified and isolated by agarose gel electrophoresis. The fragment was digested overnight at 37° C. with Not I, extracted with phenol/chloroform followed by chloroform extraction and ethanol precipitation. Plasmid pBS19 was digested with Not I, treated with calf intestinal phosphatase and the linearized plasmid was purified by agarose gel electrophoresis. The Not I digested, PCR amplified fragment of pTE11 described above was ligated into the linearized pBS19 and the ligation mixture used to transform competent Xl-1 cells. A clone in which the soybean palmitoyl-ACP cDNA was oriented in the antisense direction with respect to the beta-conglycinin promoter was identified by digestion with Hind III. The antisense orientation releases fragments of 1.6 and 1.9 kB while the sense orientation releases fragments of 1.15 and 2.3 kB. The antisense soybean palmitoyl-ACP thioesterase plasmid was designated pTC3 and the sense oriented plasmid was designated pTC4.

Transformation Of Somatic Soybean Embryo Cultures

Soybean embryogenic suspension cultures were maintained in 35 mL liquid media (SB55 or SBP6, MATERIALS AND METHODS) on a rotary shaker, 150 rpm, at 28° C. with mixed fluorescent and incandescent lights on a 16:8 h day/night schedule. Cultures were subcultured every four weeks by inoculating approximately 35 mg of tissue into 35 mL of liquid medium.

Soybean embryogenic suspension cultures were transformed with pTC3 by the method of particle gun bombardment (see Kline et al. (1987) Nature (London) 327:70). A DuPont Biolistic PDS1000/HE instrument (helium retrofit) was used for these transformations.

To 50 mL of a 60 mg/mL 1 mm gold particle suspension was added (in order); 5 uL DNA(1 ug/uL), 20 uL spermidine (0.1 M), and 50 uL $CaCl_2$ (2.5 M). The particle preparation was agitated for 3 min, spun in a microfuge for 10 sec and the supernatant removed. The DNA-coated particles were then washed once in 400 uL 70% ethanol and are suspended in 40 uL of anhydrous ethanol. The DNA/particle suspension was sonicated three times for 1 sec each. Five uL of the DNA-coated gold particles were then loaded on each macro carrier disk.

Approximately 300–400 mg of a four week old suspension culture was placed in an empty 60×15 mm petri dish and the residual liquid removed from the tissue with a pipette. For each transformation experiment, approximately 5–10 plates of tissue were normally bombarded. Membrane rupture pressure was set at 1000 psi and the chamber was evacuated to a vacuum of 28 inches of mercury. The tissue was placed approximately 3.5 inches away from the retaining screen and bombarded three times. Following bombardment, the tissue was placed back into liquid and cultured as described above.

Eleven days post bombardment, the liquid media was exchanged with fresh SB55 containing 50 mg/mL hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as independent transformation event. These suspensions can then be maintained as suspensions of embryos clustered in an immature developmental stage through subculture or regenerated into whole plants by maturation and germination of individual somatic embryos.

Transformed embryogenic clusters were removed from liquid culture and placed on a solid agar media (SB103, MATERIALS AND METHODS) containing no hormones or antibiotics. Embryos were cultured for four weeks at 26° C. with mixed fluorescent and incandescent lights on a 16:8 h day/night schedule before analysis.

Analysis Of Transgenic Glycine Max Embryos Containing An Antisense Palmitoyl-ACP Thioesterase Construct The vector pTC3 containing the soybean palmitoyl-ACP thioesterase cDNA, in the antisense orientation, under the control of the soybean beta-conglycinin promoter as described above gave rise to seven mature embryo lines. A culture of the embryo line used for transformation was carried through culture to mature embryos without transformation or selection to serve as a fatty acid profile control line. Fatty acid analysis was performed by gas chromatography of the fatty acyl methyl esters essentially as described by Browse et al., (Anal. Biochem. (1986) 152:141–145) except that 2.5% $H_2SO_4$ in methanol was used as the methylation reagent and samples were heated for 1.5 h at 80° C. to effect the methanolysis of the embryo lipids using single, mature embryos as the tissue source. Nine to ten embryos from each transformed line and 5 embryos from the untransformed control were analyzed and the results are shown in Table 3.

TABLE 3

Fatty acids in control soybean embryos and in soybean embryos transformed with a vector expressing the soybean palmitoyl-ACP thioesterase in the antisense orientation

| EMBRYO LINE | EMBRYO NO. | FATTY ACID AS % OF TOTAL FATTY ACIDS | | | | |
|---|---|---|---|---|---|---|
| | | 16:0 | 18:0 | 18:1 | 18:2 | 18:3 |
| 2872 control | 1 | 12.7 | 4.6 | 20.8 | 53.1 | 7.9 |
| 2872 control | 2 | 13.8 | 3.1 | 12.0 | 58.0 | 12.0 |
| 2872 control | 3 | 15.9 | 3.9 | 11.2 | 53.9 | 13.9 |
| 2872 control | 4 | 14.5 | 2.9 | 13.9 | 57.7 | 9.2 |
| 2872 control | 5 | 15.8 | 4.4 | 13.4 | 51.8 | 12.4 |
| 353/3/1 | 1 | 6.4 | 2.1 | 11.3 | 63.1 | 17.0 |
| 353/3/1 | 2 | 13.3 | 3.0 | 14.5 | 53.9 | 14.8 |
| 353/3/1 | 3 | 6.9 | 2.0 | 11.2 | 62.9 | 16.9 |
| 353/3/1 | 4 | 12.1 | 2.8 | 9.6 | 55.8 | 19.6 |
| 353/3/1 | 5 | 5.8 | 1.9 | 12.3 | 64.1 | 15.4 |
| 353/3/1 | 6 | 10.1 | 2.3 | 11.8 | 57.3 | 17.7 |
| 353/3/1 | 7 | 3.9 | 2.0 | 17.9 | 64.1 | 12.0 |
| 353/3/1 | 8 | 8.2 | 2.4 | 11.0 | 61.1 | 16.4 |
| 353/3/1 | 9 | 8.0 | 2.4 | 10.5 | 59.9 | 18.3 |
| 353/3/1 | 10 | 5.1 | 1.9 | 13.2 | 66.8 | 12.8 |
| 353/3/2 | 1 | 6.3 | 2.0 | 12.0 | 62.2 | 17.4 |
| 353/3/2 | 2 | 9.0 | 2.5 | 11.1 | 60.5 | 16.8 |
| 353/3/2 | 3 | 8.3 | 2.1 | 11.0 | 60.3 | 16.4 |
| 353/3/2 | 4 | 15.1 | 2.9 | 10.1 | 51.8 | 19.4 |
| 353/3/2 | 5 | 6.4 | 2.1 | 15.5 | 60.3 | 15.5 |
| 353/3/2 | 6 | 16.1 | 2.9 | 11.1 | 53.5 | 15.9 |
| 353/3/2 | 7 | 7.6 | 2.0 | 10.3 | 64.5 | 15.0 |
| 353/3/2 | 8 | 5.5 | 2.1 | 12.1 | 64.6 | 15.7 |
| 353/3/2 | 9 | 15.9 | 3.0 | 9.5 | 51.8 | 19.1 |
| 353/3/2 | 10 | 5.8 | 2.0 | 12.8 | 63.7 | 14.9 |
| 353/3/3 | 1 | 7.6 | 2.5 | 10.9 | 61.2 | 15.9 |
| 353/3/3 | 2 | 5.4 | 4.1 | 20.4 | 40.2 | 7.9 |
| 353/3/3 | 3 | 5.2 | 1.9 | 12.6 | 67.2 | 12.4 |
| 353/3/3 | 4 | 4.5 | 2.0 | 28.8 | 54.7 | 9.1 |
| 353/3/3 | 5 | 6.7 | 1.8 | 11.7 | 62.1 | 16.1 |
| 353/3/3 | 6 | 6.0 | 1.5 | 10.3 | 63.2 | 17.3 |
| 353/3/3 | 7 | 6.6 | 2.5 | 9.4 | 65.4 | 15.0 |
| 353/3/3 | 8 | 13.2 | 2.9 | 21.6 | 49.9 | 11.6 |
| 353/3/3 | 9 | 13.4 | 3.2 | 16.4 | 52.5 | 12.7 |
| 357/1/1 | 1 | 8.3 | 2.1 | 12.3 | 63.7 | 12.8 |
| 357/1/1 | 2 | 11.1 | 2.8 | 11.1 | 59.3 | 14.2 |
| 357/1/1 | 3 | 7.5 | 2.1 | 14.1 | 63.1 | 12.2 |
| 357/1/1 | 4 | 7.7 | 2.4 | 13.8 | 62.7 | 12.4 |
| 357/1/1 | 5 | 14.2 | 3.0 | 10.5 | 58.2 | 12.7 |
| 357/1/1 | 6 | 11.8 | 2.5 | 11.3 | 60.7 | 12.7 |
| 357/1/1 | 7 | 13.8 | 3.2 | 10.1 | 56.1 | 14.8 |
| 357/1/1 | 8 | 6.3 | 1.6 | 12.8 | 65.8 | 12.4 |
| 357/1/1 | 9 | 10.5 | 2.8 | 11.2 | 57.5 | 16.7 |
| 357/1/1 | 10 | 7.2 | 1.9 | 13.8 | 62.1 | 14.1 |
| 357/1/2 | 1 | 3.4 | 1.6 | 18.6 | 64.6 | 11.8 |
| 357/1/2 | 2 | 3.7 | 1.5 | 19.0 | 65.1 | 11.6 |
| 357/1/2 | 3 | 5.2 | 1.4 | 21.6 | 56.4 | 15.5 |
| 357/1/2 | 4 | 3.9 | 1.5 | 12.7 | 69.5 | 12.4 |
| 357/1/2 | 5 | 4.9 | 1.6 | 12.2 | 68.3 | 12.9 |
| 357/1/2 | 6 | 4.3 | 2.0 | 14.3 | 66.2 | 13.0 |
| 357/1/2 | 7 | 10.5 | 2.5 | 12.9 | 57.7 | 16.2 |
| 357/1/2 | 8 | 6.4 | 1.8 | 24.7 | 53.4 | 13.7 |
| 357/1/2 | 9 | 11.8 | 2.3 | 9.0 | 57.1 | 19.4 |
| 357/1/2 | 10 | 3.1 | 1.4 | 14.8 | 62.3 | 12.1 |
| 357/1/3 | 1 | 11.5 | 2.3 | 9.7 | 61.5 | 14.8 |
| 357/1/3 | 2 | 9.9 | 2.3 | 9.5 | 64.2 | 14.0 |
| 357/1/3 | 3 | 12.7 | 2.9 | 13.5 | 57.3 | 13.5 |
| 357/1/3 | 4 | 13.9 | 3.0 | 14.3 | 50.1 | 18.7 |
| 357/1/3 | 5 | 14.7 | 3.0 | 13.0 | 53.0 | 16.3 |
| 357/1/3 | 6 | 11.8 | 2.4 | 9.9 | 58.3 | 17.7 |
| 357/1/3 | 7 | 11.3 | 2.3 | 10.1 | 60.6 | 15.1 |
| 357/1/3 | 8 | 11.7 | 2.4 | 9.9 | 61.3 | 14.2 |
| 357/1/3 | 9 | 14.4 | 2.5 | 5.5 | 63.3 | 14.3 |
| 357/1/3 | 10 | 9.6 | 2.2 | 18.7 | 57.0 | 12.4 |
| 357/5/1 | 1 | 4.0 | 1.3 | 17.7 | 63.1 | 13.3 |
| 357/5/1 | 2 | 3.8 | 1.3 | 16.9 | 65.0 | 12.4 |
| 357/5/1 | 3 | 2.9 | 1.8 | 17.6 | 65.4 | 11.6 |

TABLE 3-continued

Fatty acids in control soybean embryos and in soybean embryos transformed with a vector expressing the soybean palmitoyl-ACP thioesterase in the antisense orientation

| EMBRYO LINE | EMBRYO NO. | FATTY ACID AS % OF TOTAL FATTY ACIDS | | | | |
|---|---|---|---|---|---|---|
| | | 16:0 | 18:0 | 18:1 | 18:2 | 18:3 |
| 357/5/1 | 4 | 4.1 | 1.4 | 13.6 | 66.0 | 14.0 |
| 357/5/1 | 5 | 2.8 | 1.8 | 17.0 | 67.3 | 10.9 |
| 357/5/1 | 6 | 6.3 | 1.9 | 14.3 | 61.2 | 15.5 |
| 357/5/1 | 7 | 3.4 | 1.0 | 14.9 | 68.9 | 11.1 |
| 357/5/1 | 8 | 4.5 | 1.5 | 17.0 | 62.4 | 14.0 |
| 357/5/1 | 9 | 2.9 | 0.9 | 14.5 | 70.5 | 10.6 |
| 357/5/1 | 10 | 3.1 | 1.1 | 14.9 | 69.1 | 11.0 |

The average palmitate content of six of the seven transformed lines is significantly less than that of the control embryo line. In each of these six lines, the average stearate content is also less than the control average. This result is expected if the palmitoyl-ACP thioesterase is responsible for the release of all or part of the palmitate that is incorporated into triacylglyceride and if the antisense construction has reduced the amount of palmitoyl-ACP thioesterase produced. Since the stearate content of the lines is decreased rather than increased in correspondence with the decreased palmitate, the following may be inferred: The capacity to elongate palmitoyl-ACP to stearoyl-ACP must be sufficient to convert the increased flux to stearate, and the capacity to desaturate stearoyl-ACP to oleoly-ACP must also be sufficient to convert the increased flux to oleate. These two events lead to a significant decrease in the total saturated fatty acids produced in the transformed embryos. It may also be inferred that the oleate desaturating capacity is present in excess of the substrate supplied to it since most of the carbon which was not removed from the ACP synthetic track is found in the linoleate fraction.

This is seen most clearly in a comparison of lines 357/1/3 and 357/5/1. Line 357/1/3 was transformed but shows little or no alteration in fatty acid phenotype while line 357/5/1 is quite uniform among all tested embryos in producing an altered fatty acid phenotype. The average palmitic acid content of the lipid in line 357/5/1 is 3.2 fold less than that of line 357/1/3 and the average stearic acid content of 357/1/3 is 1.8 fold less than that of line 357/5/1. The combined saturated fatty acid decrease is 12.2% of the total fatty acid, and of that 12.2%, nearly all (11.7%) can be accounted for as increased oleate and linoleate.

Thus, the combined effect is a soybean embryo line with 65% less saturated fatty acid and with increased monounsaturated and polyunsaturated fatty acid.

From this data we conclude that reduction of the amount of palmitoyl-ACP thioesterase expressed in developing soybean seeds will lead to the production of soybean oil with reduced saturated fatty acid content. The variation in the amount of antisense effect observed between embryos but within a transformed line seen in Table 3 is a characteristic of this transformation system which is explained more fully below. The relation between data taken from the immature embryos and seeds from the zygotic embryos produced on plants regenerated from these somatic embryos is dicussed below.

The Fatty Acid Phenotype Resulting From Antisense Or Co-Suppression Inhibition Of Gene Expression In Soybean Somatic Embryos Is Predictive Of The Fatty Acid Phenotype Of Seeds Of Plants Regenerated From Those Embryos Mature somatic soybean embryos are a good model for zygotic embryos. While in the globular embryo state in liquid culture, somatic soybean embryos contain very low amounts of triacylglycerol or storage proteins, typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, alpha' subunit of beta-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for alpha'-subunit of beta-conglycinin, kunitz trypsin inhibitor 3 and seed lectin become very abundant messages in the total mRNA population. On this basis the somatic soybean embryo system behaves very similarly to maturing zygotic soybean embryos in vivo, and is therefore a good and rapid model system for analyzing the phenotypic effects of modifying the expression of genes in the fatty acid biosynthesis pathway.

Most importantly, the model system is also predictive of the fatty acid composition of seeds from plants derived from transgenic embryos. This is illustrated with two different antisense constructs in two different types of experiment and in a similar co-suppression experiment:

Liquid culture globular embryos transformed with a chimeric gene consisting of soybean microsomal delta-15 desaturase (experiment 1, WO 9311245) or soybean microsomal delta-12 desaturase (experiment 2) in antisense orientation under the control of a seed-specific promoter (beta-conglycinin promoter) gave rise to mature embryos. The fatty acid content of mature somatic embryos from lines transformed with vector only (control) and the vector containing the antisense chimeric genes as well as of seeds of plants regenerated from them was determined. In experiment 1, one set of embryos from each line was analyzed for fatty acid content and another set of embryos from that same line was regenerated into plants. In experiment 2, different lines, containing the same antisense construct, were used for fatty acid analysis in somatic embryos and for regeneration into plants. In experiment 1, in all cases where a reduced 18:3 content was seen in a transgenic embryo line, compared with the control, a reduced 18:3 content was also observed in segregating seeds of plants derived from that line, when compared with the control seed (Table 4).

In experiment 2, about 55% of the transformed embryo lines showed an increased 18:1 content when compared with control lines (Table 5). Soybean seeds, of plants regenerated from different somatic embryo lines containing the same antisense construct, had a similar frequency (53%) of high oleate transformants as the somatic embryos (Table 5). On occasion, an embryo line may be chimeric. That is, 10–70% of the embryo in a line may not contain the transgene. The remaining embryos which do contain the transgene, have been found in all cases to be clonal. In such a case, plants with both wild type and transgenic phenotypes may be regenerated from a single, transgenic line, even if most of the embryos analyzed from that line had a transgenic phenotype. An example of this is shown in Table 6 in which, of 5 plants regenerated from a single embryo line, 3 have a high oleic phenotype and two were wild type. In most cases, all the plants regenerated from a single transgenic line will have seeds containing the transgene.

TABLE 4

Percent 18:3 Content of Embryos And Seeds Of Control and Delta-15 Antisense Construct Transgenic Soybean Lines

| Transformant Line | Embyro average (SD n = 10) | Seed average* (SD, n = 10) |
|---|---|---|
| Control | 12.1 (2.6) | 8.9 (0.8) |
| Δ15 antisense, line 1 | 5.6 (1.2) | 4.3 (1.6) |
| Δ15 antisense, line 2 | 8.9 (2.2) | 2.5 (1.8) |
| Δ15 antisense, line 3 | 7.3 (1.1) | 4.9 (1.9) |
| Δ15 antisense, line 4 | 7.0 (1.9) | 2.4 (1.7) |
| Δ15 antisense, line 5 | 8.5 (1.9) | 4.5 (2.2) |
| Δ15 antisense, line 6 | 7.6 (1.6) | 4.6 (1.6) |

*[Seeds which were segregating with wild-type phenotype and without a copy of the transgene are not included in these averages]

TABLE 5

Oleate Levels in Somatic Embryos And Seeds Of Regenerated Soybeans Transformed With or Without Delta-12 Desaturase Antisense Construct

| Vector | # of lines | # of lines with high 18:1 | Average# % 18:1 |
|---|---|---|---|
| Somatic embryos: | | | |
| Control | 19 | 0 | 12.0 |
| D 12 antisense | 20 | 11 | 35.3 |
| Seeds of regenerated plants: | | | |
| Control | 6 | 0 | 18.2 |
| D 12 antisense | 17 | 9 | 44.4 |

*average 18:1 of transgenics is the average of all embryos or seeds transformed with the delta-12 antisense construct in which at least one embryo or seed from that line had an 18:1 content greater that 2 standard deviations from the control value (12.0 in embryos, 18.2 in seeds). The control average is the average of embryos or seeds which do not contain any transgenic DNA but have been treated in an identical manner to the transgenics

TABLE 6

Mean of 15–20 seeds from 5 different plants regenerated from a single embryo line. Only plants #2, 9 and 11 have seeds with a high 1B:1 phenotype

| Line 4 Plant # | Average seed 18:1% | Highest seed 18:1% |
|---|---|---|
| 1 | 18.0 | 26.3 |
| 2 | 33.6 | 72.1 |
| 7 | 13.6 | 21.2 |
| 9 | 32.9 | 57.3 |
| 11 | 24.5 | 41.7 |

In a similar experiment, 75% of the coding region (begininng at the 5' end) of the delta-12 desaturase sequence and of the delta-15 desaturase sequence were each placed behind the b-conglycinin promoter in a single construction for soybean transformation as described above. As in experiment 2 above, seperate embryo sets were used for analysis at the embryo stage and regeneration into fertile plants. The average 18:1 and 18:3 content in five embryos from each of 7 transformed lines is given in Table 7. Of the 7 lines two clearly have elevated levels of 18:1 as would be expected of embryos in which the conversion of 18:1 to 18:2 by delta-12 desaturase is limited due to decreased expression of the enzyme. In these same lines there is a slight decrease in the 18:3 content, indicative of a decreased delta-15 desaturase activity.

TABLE 7

The 18:1 and 18:3 content in somatic embryos from seven lines transfromed with a combined Delta-12 and Delta-15 co-suppression construct.
Values are the mean of five individual embryos

| Line | %18:1 | %18:3 |
| --- | --- | --- |
| 561/1/1 | 45.1 | 10.1 |
| 561/1/2 | 18.4 | 13.8 |
| 561/1/3 | 10.7 | 15.2 |
| 561/4/1 | 39.3 | 13.4 |
| 561/4/2 | 18.7 | 13.2 |
| 561/4/4 | 19.7 | 14.1 |
| 561/4/5 | 14.6 | 16.1 |
| 561/4/6 | 43.9 | 12.9 |

Twenty, fertile soybean plants were regenerated from somatic embryos transformed with the combined D12/D15 desaturase co-suppression construction described above. Five single seeds from each plant were analyzed and of the twenty lines, two showed bulk fatty acid profiles which suggested that both the D 12 and D 15 desaturase activities were decreased. The first seeds from transformed plants should be genetically segregating for the transgene so single seeds from these two lines were analyzed to derive an estimate of the number of transgene loci contributing to the fatty acid phenotype. Ninty nine seeds of line 557-2-8-1 were analyzed and 137 seeds of line 557-2-8-2 were analyzed. The fatty acid profile classes from both lines were consistent with two transgenic loci contributing to the phenotype. The average fatty acid profile of the seeds which were judged to be in the high segregant class are given in Table 8 for both of these lines.

Table 8

The average fatty acid profiles (as % of total fatty acids) for the probable double homozygous seeds from two lines segregating for co-suppression transgenes for the Δ12 and Δ15 desaturases. The data are the mean of 10 single seed profiles for line 557-2-8-1 and 13 single seed profiles for line 557-2-8-2. The profile from a non-transformed line grown along with the transformed lines in shown for comparison.

| Line | 16:0 | 18:0 | 18:1 | 18:2 | 18:3 |
| --- | --- | --- | --- | --- | --- |
| 557-2-8-1 | 8.6 | 2.1 | 82.5 | 2.5 | 4.2 |
| 557-2-8-2 | 8.3 | 2.1 | 82.0 | 2.2 | 5.0 |
| non-transformed | 13.3 | 2.4 | 17.4 | 52.3 | 19.2 |

As with the antisense constructions, the fatty acid profiles observed in the somatic embryos is predictive of the type and magnitude of alteration in fatty acid profile which will be obtained from the seeds of fertile plants transformed with the same construction as the somatic embryos. Thus, we conclude that an altered fatty acid phenotype observed in a transgenic, mature somatic embryo line is predictive of an altered fatty acid composition of seeds of plants derived from that line.

Analysis Of Transgenic Glycine Max Embryos Containing A Palmitoyl-ACP Thioesterase Construct In The Sense Orientation The vector pTC4 containg the soybean palmitoyl-ACP thioesterase cDNA, in the sense orientation, under the control of the soybean beta-conglycinin promoter as described above gave rise to six mature embryo lines in the soybean somatic embryo system. From 6 to 10 embryos from each of these lines were analyzed for relative content of each fatty acid as described above. The results are shown in Table 9.

TABLE 9

Fatty acids in soybean embryos transformed with a vector expressing the soybean palmitoyl-ACP thioesterase in the sense orientation

| | | FATTY ACID AS % OF TOTAL FATTY ACIDS | | | | |
| --- | --- | --- | --- | --- | --- | --- |
| EMBRYO LINE | EMBRYO NO. | 16:0 | 18:0 | 18:1 | 18:2 | 18:3 |
| 361/1/1 | 1 | 14.8 | 3.3 | 10.9 | 54.9 | 14.5 |
| 361/1/1 | 2 | 13.1 | 2.7 | 10.2 | 56.9 | 16.3 |
| 361/1/1 | 3 | 11.7 | 3.0 | 14.5 | 57.4 | 12.4 |
| 361/1/1 | 4 | 10.0 | 3.1 | 24.1 | 50.4 | 11.6 |
| 361/1/1 | 5 | 10.9 | 2.6 | 17.9 | 54.6 | 12.9 |
| 361/1/1 | 6 | 10.5 | 3.1 | 27.5 | 47.3 | 10.6 |
| 361/1/1 | 7 | 9.8 | 3.4 | 31.5 | 43.9 | 10.5 |
| 361/1/1 | 8 | 10.5 | 3.4 | 23.7 | 50.0 | 11.0 |
| 361/1/1 | 9 | 15.0 | 3.5 | 9.6 | 57.5 | 13.4 |
| 361/1/1 | 10 | 12.8 | 3.1 | 18.7 | 52.6 | 12.0 |
| 361/1/2 | 1 | 3.9 | 2.3 | 16.1 | 66.7 | 10.1 |
| 361/1/2 | 2 | 10.2 | 3.3 | 26.4 | 47.5 | 11.7 |
| 361/1/2 | 3 | 4.7 | 2.3 | 20.8 | 60.0 | 11.4 |
| 361/1/2 | 4 | 3.7 | 2.5 | 27.0 | 56.9 | 8.8 |
| 361/1/2 | 5 | 3.9 | 3.1 | 37.7 | 45.8 | 8.4 |
| 361/1/2 | 6 | 3.8 | 2.0 | 16.6 | 67.2 | 9.4 |
| 361/2/1 | 1 | 13.1 | 2.9 | 10.8 | 55.8 | 16.7 |
| 361/2/1 | 2 | 12.0 | 2.5 | 11.2 | 57.3 | 16.2 |
| 361/2/1 | 3 | 13.5 | 3.0 | 13.2 | 55.2 | 3.6 |
| 361/2/1 | 4 | 13.5 | 2.8 | 11.6 | 56.4 | 14.9 |
| 361/2/1 | 5 | 15.3 | 3.0 | 7.0 | 56.9 | 17.0 |
| 361/2/1 | 6 | 13.1 | 2.2 | 10.1 | 59.0 | 14.1 |
| 361/2/1 | 7 | 13.4 | 2.9 | 12.5 | 56.9 | 13.6 |
| 361/2/1 | 8 | 15.1 | 4.0 | 13.9 | 49.4 | 16.5 |
| 361/2/1 | 9 | 15.7 | 3.3 | 11.2 | 54.6 | 13.8 |
| 361/2/1 | 10 | 13.1 | 2.7 | 11.5 | 58.0 | 13.8 |
| 361/2/2 | 1 | 4.4 | 1.5 | 40.3 | 40.9 | 12.9 |
| 361/2/2 | 2 | 29.2 | 3.6 | 12.8 | 42.2 | 11.2 |
| 361/2/2 | 3 | 2.4 | 1.0 | 37.1 | 45.0 | 14.4 |
| 361/2/2 | 4 | 1.7 | 0.7 | 46.6 | 37.3 | 14.4 |
| 361/2/2 | 5 | 3.4 | 1.5 | 31.2 | 51.6 | 12.4 |
| 361/2/2 | 6 | 4.1 | 1.4 | 29.6 | 46.2 | 20.1 |
| 361/2/2 | 7 | 3.7 | 1.2 | 37.8 | 40.1 | 18.4 |
| 361/2/2 | 8 | 3.6 | 1.5 | 35.4 | 46.2 | 13.3 |
| 361/2/2 | 9 | 5.6 | 2.4 | 41.1 | 31.7 | 17.6 |
| 361/5/1 | 1 | 13.7 | 2.5 | 11.8 | 57.8 | 13.4 |
| 361/5/1 | 2 | 27.2 | 3.6 | 9.8 | 46.3 | 11.8 |
| 361/5/1 | 3 | 16.8 | 2.8 | 12.8 | 53.4 | 13.4 |
| 361/5/1 | 4 | 14.6 | 2.5 | 11.4 | 56.6 | 14.2 |
| 361/5/1 | 5 | 25.9 | 4.0 | 13.8 | 42.9 | 12.5 |
| 361/5/1 | 6 | 25.1 | 3.3 | 10.3 | 49.3 | 11.0 |
| 361/5/1 | 7 | 27.2 | 3.0 | 4.9 | 48.6 | 15.6 |
| 361/5/1 | 8 | 27.0 | 3.8 | 9.8 | 44.9 | 13.1 |
| 361/5/1 | 9 | 28.5 | 3.5 | 10.1 | 45.8 | 11.2 |
| 361/5/1 | 10 | 22.8 | 4.1 | 14.0 | 46.1 | 11.9 |
| 361/5/2 | 1 | 28.7 | 3.5 | 9.8 | 44.3 | 12.7 |
| 361/5/2 | 2 | 31.0 | 3.5 | 8.7 | 43.5 | 12.4 |
| 361/5/2 | 3 | 20.2 | 3.7 | 9.8 | 51.0 | 14.2 |
| 361/5/2 | 4 | 26.6 | 3.4 | 12.9 | 44.2 | 11.8 |
| 361/5/2 | 5 | 27.3 | 3.5 | 9.3 | 44.4 | 12.4 |
| 361/5/2 | 6 | 25.9 | 3.5 | 11.6 | 45.2 | 12.7 |
| 361/5/2 | 7 | 25.6 | 3.7 | 9.2 | 46.5 | 13.8 |
| 361/5/2 | 8 | 25.3 | 3.7 | 11.2 | 46.5 | 12.3 |
| 361/5/2 | 9 | 24.8 | 3.8 | 9.6 | 46.4 | 14.5 |
| 361/5/2 | 10 | 26.6 | 3.7 | 9.8 | 44.9 | 14.0 |

As is often the case when increasing the expression of an mRNA which is endogenous to the targeted tissue, the effects of both over-expression of the resulting enzyme and under expresssion of the enzyme due to co-supression are seen in this experiment. While lines 361/1/1 and 361/2/1 have fatty acid profiles very similar to control lines (shown in Table 9), most of the embryos in line 361/1/2 have levels of palmitic acid which are about 3 fold lower than controls or transformed lines which do not show altered fatty acid phenotype. In contrast, the palmitic acid content of all of the embryos in line 361/5/2 is increased and the average palmitic acid content is 26.2% or 1.8 times the average control embryo. Line 361/2/2 contains 8 embryos which show the co-supression phenotype (low palmitic acid) and one embryo which shows the over expression phenotype (high palmitic acid content).

In this experiment the effects of altered expression of the soybean palmitoyl-ACP thioesterase are seen in both directions, and the resulting phenotypes are as expected from the substrate specificity of the enzyme. Modulation of expression upward increases the relative palmitic acid content and downward decreases the relative palmitic acid content.

Example 4

REGULATION OF EXPRESSION OF PALMITOYL-ACP THIOESTERASE IN CANOLA

Construction Of Vectors For Transformation Of *Brassica Napus* For Reduced Expression Of Palmitoyl-ACP thioesterase In Developing Canola Seeds An extended poly A tail was removed from the canola palmitoyl-ACP thioesterase sequence contained in plasmid p5b as follows. Plasmid p5b was digested with Eco RI and Ssp I and the 1.5 kB fragment released from the pBluescript vector was isolated by agarose gel electrophoresis. The single stranded ends were filled in with Klenow fragment and dNTP's.

Canola napin promoter expression cassettes were constructed as follows: Eight oligonucleotide primers were synthesized based upon the nucleotide sequence of napin lambda clone CGN1-2 published in European Patent 255 378. The oligonucleotide sequences were:
BR42: 5'-AACATCAATGGCAGCAACTGCGGA-3' SEQ ID NO:13
BR43: 5'-GCCGGCTGGATTTGTGGCATCAT-3' SEQ ID NO:14
BR45: 5'-CTAGATCTCCATGGGTGTATGTTCTGTAG TGATG-3' SEQ ID NO:15
BR46: 5'-TCAGGCCTGTCGACCTGCGGATCA AGCAGCTTTCA-3' SEQ ID NO:16
BR47: 5'-CTAGATCTGGTACCTAGATTCCAAACGAAI ATCCT-3' SEQ ID NO:17
BR48: 5'-AACATCAGGCAAGTTAGCATTTGC-3' SEQ ID NO:18
BR49: 5'-TCAGGCCTGTCGACGAGGTCCTTCGTCAGC ATAT-3' SEQ ID NO:19
BR50: 5'-AACGAACCAATGACTTCACTGGGA-3' SEQ ID NO:20

Genomic DNA from the canola variety 'Hyola401' (Zeneca Seeds) was used as a template for PCR amplification of the napin promoter and napin terminator regions. The promoter was first amplified using primers BR42 and BR43, and reamplified using primers BR45 and BR46. Plasmid pIMC01 was derived by digestion of the 1.0 kb promoter PCR product with SalI/BglII and ligation into SalI/BamHI digested pBluescript SK+ (Stratagene). The napin terminator region was amplified using primers BR48 and BR50, and reamplified using primers BR47 and BR49. Plasmid pIMC06 was derived by digestion of the 1.2 kb terminator PCR product with SalI/BglII and ligation into SalI/BglII digested pSP72 (Promega). Using pIMC06 as a template, the terminator region was reamplified by PCR using primer BR57 5'-CCATGGGAGCTCGTCGACGAGGTCCTT CGTCACGAT-3' SEQ ID NO:21 and primer
BR58 5'-GAGCTCCCATGGAGATCTGGTACCTAG ATTCCAAAC-3' SEQ ID NO:22

Plasmid pIMC101 containing both the napin promoter and terminator was generated by digestion of the PCR product with SacI/NcoI and ligation into SacI/NcoI digested pIMC01. Plasmid pIMC101 contains a 2.2 kb napin expression cassette including complete napin 5' and 3' non-translated sequences and an introduced NcoI site at the translation start ATG. Primer
BR61 5'-GACTATGTTCTGAATTCTCA-3' SEQ ID NO:23 and primer
BR62 5'-GACAAGATCTGCGGCCGCTAAAGAGTG AAGCCGAGGCTC-3' SEQ ID NO:24
were used to PCR amplify an ~270 bp fragment from the 3' end of the napin promoter. Plasmid pIMC401 was obtained by digestion of the resultant PCR product with EcoRI/BglII and ligation into EcoRI/BglII digested pIMC 1 01. Plasmid pIMC40 1 contains a 2.2 kb napin expression cassette lacking the napin 5' non-translated sequence and includes a NotI site at the transcription start.

The oligonucleotide sequences were:

BR42 and BR43 corresponding to bases 29 to 52 (BR42) and the complement of bases 1146 to 1169 (BR43) of SEQ ID NO:8.

BR45 and BR46 corresponding to bases 46 to 66 (BR46) and the complement of bases 1028 to 1047 (BR45) of SEQ ID NO:8. In addition BR46 had bases corresponding to a Sal I site (5'-GTCGAC-3') and a few additional bases (5'-TCAGGCCT-3') at its 5' end and BR45 had bases corresponding to a Bgl II site (5'-AGATCT-3') and two (5'-CT-3') additional bases at the 5' end of the primer.

BR47 and BR48 corresponding to bases 81 to 102 (BR47) and bases 22 to 45 (BR48) of SEQ ID NO:10. In addition, BR47 had two (5'-CT-3') additional bases at the 5' end of the primer followed by bases corresponding to a Bgl II site (5'-AGATCT-3') followed by a few additional bases (5'-TCAGGCCT-3'), BR49 and BR50 corresponding to the complement of bases 1256 to 1275 (BR49) and the complement of bases 1274 to 1297 (BR50) of SEQ ID NO:10. In addition BR49 had bases corresponding to a Sal I site (5'-GTCGAC-3') and a few additional bases (5'-TCAGGCCT-3') at its 5' end.

BR57 and BR58 corresponding to the complement of bases 1258 to 1275 (BR57) and bases 81 to 93 (BR58) of SEQ ID NO:10. In addition the 5' end of BR57 had some extra bases (5'-CCATGG-3') followed by bases corresponding to a Sac I site (5'-GAGCTC-3') followed by more additional bases (5'-GTCGACGAGG-3') (SEQ ID NO:25). The 5' end of BR58 had additional bases (5'-GAGCTC-3') followed by bases corresponding to a Nco I site (5'-CCATGG-3') followed by additional bases (5' AGATCTGGTACC-3') (SEQ ID NO:26).

BR61 and BR62 corresponding to bases 745 to 764 (BR61) and bases 993 to 1013 (BR62) of SEQ ID NO:8. In addition the 5' end of BR 62 had additional bases (5'-GACA-3') followed by bases corresponding to a Bgl II site (5'-AGATCT-3') followed by a few additional bases (5'-GCGGCCGC-3').

Genomic DNA from the canola variety 'Hyola401' (Zeneca Seeds) was used as a template for PCR amplification of the napin promoter and napin terminator regions. The promoter was first amplified using primers BR42 and BR43, and reamplified using primers BR45 and BR46. Plasmid pIMC01 was derived by digestion of the 1.0 kb promoter PCR product with SalI/BglII and ligation into SalI/BamHI digested pBluescript SK+(Stratagene). The napin terminator region was amplified using primers BR48 and BR50, and reamplified using primers BR47 and BR49. Plasmid pIMC06 was derived by digestion of the 1.2 kb terminator PCR product with SalI/BglII and ligation into SalI/BglII digested pSP72 (Promega). Using pIMC06 as a template, the terminator region was reamplified by PCR using primer BR57 and primer BR58. Plasmid pIMC101 containing both the napin promoter and terminator was generated by digestion of the PCR product with SacI/NcoI and ligation into SacI/NcoI digested pIMC01. Plasmid pIMC101 contains a 2.2 kb napin expression cassette including complete napin 5' and 3' non-translated sequences and an introduced NcoI site at the translation start ATG. Primer BR61 and primer BR62 were used to PCR amplify an ~270 bp fragment from the 3' end of the napin promoter. Plasmid pIMC401 was obtained by digestion of the resultant PCR product with EcoRI/BglII and ligation into EcoRI/BglII digested pIMC101. Plasmid pIMC401 contains a 2.2 kb napin expression cassette lacking the napin 5' non-translated sequence and includes a NotI site at the transcription start.

Plasmid pIMC401 was digested with Not I and the single stranded ends filled with dNTP's and Klenow fragment. The linearized plasmid was treated with calf intestinal phosphatase. The phospatase treated and linearized plasmid was ligated to the blunted, 1.5 kB fragment of canola palmitoyl-ACP thioesterase described above. Transformation of competent E. coli cells with the ligation mixture resulted in the isolation of clones in which the plant cDNA sequence was in the sense orientation with respect to the napin promoter (pIMC29) and in the antisense orientation (pIMC30).

The vector for transformation of the antisense palmitoyl-ACP thioesterase construction under control of the napin promoter into plants using Agrobacterium tumefaciens was produced by constructing a binary Ti plasmid vector system (Bevan, (1984) Nucl. Acids Res. 12:8711–8720). One starting vector for the system, (pZS199) is based on a vector which contains: (1) the chimeric gene nopaline synthase/neomycin phosphotransferase as a selectable marker for transformed plant cells (Brevan et al. (1984) Nature 304:184–186), (2) the left and right borders of the T-DNA of the Ti plasmid (Brevan et al. (1984) Nucl. Acids Res. 12:8711–8720), (3) the E. coli lacZ α-complementing segment (Vieria and Messing (1982) Gene 19:259–267) with unique restriction endonuclease sites for Eco RI, Kpn I, Bam HI, and Sal I, (4) the bacterial replication origin from the Pseudomonas plasmid pVS1 (Itoh et al. (1984) Plasmid 11:206–220), and (5) the bacterial neomycin phosphotransferase gene from Tn5 (Berg et al. (1975) Proc. Natnl. Acad. Sci. U.S.A. 72:3628–3632) as a selectable marker for transformed A. tumefaciens. The nopaline synthase promoter in the plant selectable marker was replaced by the 35S promoter (Odell et al. (1985) Nature, 313:810–813) by a standard restriction endonuclease digestion and ligation strategy. The 35S promoter is required for efficient Brassica napus transformation as described below.

The binary vectors containing the sense and antisense palmitoyl-ACP thioesterase expression cassettes were constructed by digesting pIMC29 and pIMC30 with Sal I to release the napin:palmitoyl-ACP thioesterase cDNA:napin 3' sequence and agarose gel purification of the 3.8 kB fragments. Plasmid pZS199 was also digested with Sal I and the 3.8 kB fragments isolated from pIMC29 and pIMC30 were ligated into the linearized vector. Transformation and isolation of clones resulted in the binary vector containing the sense construct (pIMC129) and the antisense construct (pIMC130).

Agrobacterium-Mediated Transformation Of *Brassica Napus*

The binary vectors pIMC129 and pIMC130 were transferred by a freeze/thaw method (Holsters et al. (1978) Mol. Gen. Genet. 163:181–187) to the Agrobacterium strain LBA4404/pAL4404 (Hockema et al. (1983), Nature 303:179–180).

*Brassica napus* cultivar "Westar" was transformed by co-cultivation of seedling pieces with disarmed *Agrobacterium tumefaciens* strain LBA4404 carrying the the appropriate binary vector.

*B. napus* seeds were sterilized by stirring in 10% Chlorox, 0.1% SDS for thirty min, and then rinsed thoroughly with sterile distilled water. The seeds were germinated on sterile medium containing 30 mM $CaCl_2$ and 1.5% agar, and grown for six days in the dark at 24° C.

Liquid cultures of Agrobacterium for plant transformation were grown overnight at 28° C. in Minimal A medium containing 100 mg/L kanamycin. The bacterial cells were pelleted by centrifugation and resuspended at a concentration of $10^8$ cells/mL in liquid Murashige and Skoog Minimal Organic medium containing 100 μM acetosyringone.

*B. napus* seedling hypocotyls were cut into 5 mm segments which were immediately placed into the bacterial suspension. After 30 min, the hypocotyl pieces were removed from the bacterial suspension and placed onto BC-28 callus medium containing 100 μM acetosyringone. The plant tissue and Agrobacteria were co-cultivated for three days at 24° C. in dim light.

The co-cultivation was terminated by transferring the hypocotyl pieces to BC-28 callus medium containing 200 mg/L carbenicillin to kill the Agrobacteria, and 25 mg/L kanamycin to select for transformed plant cell growth. The seedling pieces were incubated on this medium for three weeks at 24° C. under continuous light.

After three weeks, the segments were transferred to BS-48 regeneration medium containing 200 mg/L carbenicillin and 25 mg/L kanamycin. Plant tissue were subcultured every two weeks onto fresh selective regeneration medium, under the same culture conditions described for the callus medium. Putatively transformed calli grow rapidly on regeneration medium; as calli reach a diameter of about 2 mm, they are removed from the hypocotyl pieces and placed on the same medium lacking kanamycin.

Shoots begin to appear within several weeks after transfer to BS-48 regeneration medium. As soon as the shoots form discernable stems, they are excised from the calli, transferred to MSV-1A elongation medium, and moved to a 16:8-h photoperiod at 24° C.

Once shoots have elongated several internodes, they are cut above the agar surface and the cut ends are dipped in Rootone. Treated shoots are planted directly into wet Metro-Mix 350 soilless potting medium. The pots are covered with plastic bags which are removed when the plants are clearly growing—after about ten days.

Plants are grown under a 16:8-h photoperiod, with a daytime temperature of 23° C. and a nightime temperature of 17° C. When the primary flowering stem begins to elongate, it is covered with a mesh pollen-containment bag to prevent outcrossing. Self-pollination is facilitated by shaking the plants several times each day, and seeds mature by about 90 days following transfer to pots.

The relative content of each of the 7 main fatty acids in the seed lipid was analyzed as follows: Twenty seeds taken at random from a sample of 25 pods from each plant were ground in 0.5 mL of 2-propanol. Twenty five μL of the resulting extract was transferred to a glass tube and the solvent evaporated under a nitrogen stream. The dry residue was subjected to methanolysis in 0.5 mL of 1% sodium methoxide in methanol at 60° C. for 1 hour. The fatty acid methyl esters produced were extracted into 1 mL of hexane and 0.5 mL of water was added to the solvent mixture to wash methanol from the hexane layer. A portion of the hexane layer was transferred to a sample vial for analysis by gas-liquid chromatography as described in Example 3 above. While seven fatty acids were analyzed, only the relative contribution of the 5 main fatty acids to the total are shown in Tables 10, 11 and 12 below.

TABLE 10

The relative contribution of 5 fatty acids to the bulk seed fatty acid content in segregating canola plants transformed with pIMC129 containing the canola palmitoyl-ACP thioesterase in the sense orientation to the Napin promotor

| TRANSFORMANT NO. | FATTY ACID AS % OF TOTAL FATTY ACIDS | | | | |
|---|---|---|---|---|---|
| | 16:0 | 18:0 | 18:1 | 18:2 | 18:3 |
| 129-511 | 4.1 | 1.4 | 67.9 | 19.0 | 5.9 |
| 129-186 | 4.2 | 1.4 | 66.5 | 20.0 | 5.9 |
| 129-230 | 4.2 | 1.2 | 63.9 | 21.0 | 7.9 |
| 129-258 | 4.0 | 1.4 | 57.2 | 25.5 | 10.0 |
| 129-107 | 4.7 | 1.7 | 59.0 | 24.1 | 8.4 |
| 129-457 | 4.3 | 1.3 | 62.0 | 22.8 | 7.7 |
| 129-381 | 4.2 | 1.1 | 58.0 | 24.8 | 10.0 |
| 129-515 | 4.4 | 1.3 | 63.4 | 21.8 | 7.5 |
| 129-122 | 4.0 | 1.4 | 63.0 | 21.4 | 8.4 |
| 129-176 | 4.1 | 1.4 | 65.7 | 19.6 | 7.5 |
| 129-939 | 4.4 | 1.7 | 64.8 | 19.2 | 8.2 |
| 129-303 | 4.2 | 1.5 | 62.3 | 21.4 | 9.4 |
| 129-208 | 3.8 | 1.4 | 66.9 | 18.0 | 8.2 |
| 129-835 | 4.3 | 1.6 | 58.0 | 24.5 | 9.7 |
| 129-659 | 4.0 | 1.6 | 60.8 | 22.2 | 10.0 |
| 129-44 | 4.2 | 1.8 | 66.0 | 18.4 | 7.7 |
| 129-756 | 3.9 | 1.6 | 60.0 | 22.4 | 10.0 |
| 129-30 | 4.0 | 1.7 | 64.8 | 18.7 | 9.6 |
| 129-340 | 3.8 | 1.7 | 67.1 | 17.4 | 7.9 |
| 129-272 | 3.9 | 1.8 | 59.4 | 21.3 | 12.0 |
| 129-358 | 4.2 | 1.5 | 60.7 | 20.8 | 11.0 |
| 129-223 | 4.3 | 1.6 | 63.4 | 20.6 | 8.3 |
| 129-314 | 4.1 | 2.0 | 61.8 | 21.4 | 9.4 |
| 129-657 | 4.2 | 1.8 | 64.8 | 18.3 | 9.1 |
| 129-151 | 4.2 | 1.4 | 62.5 | 20.8 | 9.2 |
| 129-40 | 4.3 | 1.6 | 63.8 | 20.8 | 7.8 |
| 129-805 | 4.4 | 2.2 | 61.6 | 19.4 | 10.0 |
| 129-44 | 4.1 | 1.6 | 64.2 | 19.1 | 8.7 |
| 129-288 | 3.5 | 1.5 | 65.1 | 18.9 | 8.9 |
| 129-833 | 4.2 | 1.7 | 58.8 | 23.6 | 9.4 |
| 129-889 | 4.6 | 2.8 | 57.6 | 26.4 | 9.5 |
| 129-247 | 5.7 | 1.5 | 52.8 | 27.2 | 13.0 |
| 129-355 | 4.3 | 2.3 | 66.0 | 19.1 | 6.3 |
| 129-631 | 4.5 | 2.3 | 66.7 | 19.4 | 5.6 |
| 129-73 | 5.0 | 2.5 | 65.4 | 20.8 | 6.4 |
| 129-407 | 3.9 | 1.5 | 65.4 | 21.2 | 6.1 |
| westar | 4.0 | 1.7 | 64.0 | 19.7 | 8.5 |

None of the transformed plants analyzed have fatty acid profiles which are markedly different from that expected in canola seeds. Plants number 129-805, 129-889, and 129-73 are slightly elevated in their saturated fatty acid content and may represent lines with a low amount of over expression. Since the transformation event gives rise to a plant which is heterozygous for the introduced transgene, the seed from these plants is segregating with respect to the transgene copy number. If, as expected, the fatty acid phenotype is additive with respect to the transgene copy number, the full effect cannot be seen in bulk seed population until the second generation past transformation. Further analysis will be done on subsequent generations of plants with modest increases in saturated fatty acid content.

There is no strong evidence for the low palmitate phenotype expected from a co-supressing transformant. In contrast to soybean however, co-supression in canola is a rare transformation event. In our experience with other genes in the fatty acid biosynthetic pathway, as many as 200 transformed lines have been required to observe a strong co-supression phenotype.

TABLE 11

The relative contribution of 5 fatty acids to the bulk seed fatty acid content in segregating canola plants transformed with pIMC130 containing the canola palmitoyl-ACP thioesterase in the antisense orientation to the Napin promotor

| TRANSFORMANT NO. | FATTY ACID AS % OF TOTAL FATTY ACIDS | | | | |
|---|---|---|---|---|---|
| | 16:0 | 18:0 | 18:1 | 18:2 | 18:3 |
| 130-220 | 4.0 | 1.7 | 65.5 | 20.1 | 6.4 |
| 130-527 | 4.1 | 1.7 | 62.6 | 19.7 | 10.0 |
| 130-529 | 4.4 | 1.7 | 69.6 | 17.4 | 4.6 |
| 130-347 | 4.0 | 1.4 | 64.8 | 21.3 | 6.1 |
| 130-738 | 4.9 | 1.5 | 56.6 | 27.4 | 7.3 |
| 130-317 | 4.2 | 1.4 | 62.4 | 22.7 | 7.6 |
| 130-272 | 4.8 | 1.6 | 62.7 | 23.2 | 6.4 |
| 130-412 | 4.4 | 1.4 | 63.7 | 22.3 | 6.7 |
| 130-119 | 3.9 | 1.1 | 59.7 | 25.7 | 7.9 |
| 130-257 | 5.0 | 1.8 | 62.1 | 20.5 | 8.8 |
| 130-677 | 4.8 | 1.2 | 53.6 | 28.6 | 10.0 |
| 130-310 | 4.6 | 1.6 | 61.6 | 23.0 | 7.3 |
| 130-323 | 4.0 | 2.0 | 67.8 | 16.9 | 7.4 |
| 130-699 | 4.1 | 1.1 | 62.8 | 23.4 | 6.8 |
| 130-478 | 5.0 | 2.0 | 57.0 | 23.4 | 11.0 |
| 130-651 | 4.4 | 1.6 | 66.0 | 19.2 | 7.7 |
| 130-126 | 3.4 | 1.7 | 68.4 | 16.2 | 8.6 |
| 130-465 | 5.1 | 1.9 | 58.5 | 24.1 | 10.0 |
| 130-234 | 4.2 | 1.6 | 64.2 | 20.9 | 7.8 |
| 130-661 | 4.4 | 1.4 | 60.6 | 22.8 | 9.6 |
| 130-114 | 4.2 | 1.4 | 65.2 | 19.7 | 7.8 |
| 130-305 | 4.6 | 1.6 | 58.6 | 23.9 | 10.0 |
| 130-240 | 4.1 | 1.4 | 69.1 | 17.4 | 6.5 |
| 130-660 | 4.1 | 1.4 | 67.0 | 18.5 | 7.2 |
| 130-350 | 4.1 | 1.5 | 62.5 | 21.1 | 9.8 |
| 130-36 | 4.1 | 1.9 | 61.4 | 21.7 | 8.9 |
| 130-527 | 4.1 | 1.5 | 64.7 | 19.0 | 9.0 |
| 130-33 | 4.0 | 1.1 | 62.6 | 22.1 | 9.1 |
| westar | 4.0 | 1.7 | 64.0 | 19.7 | 8.5 |

The average palmitic acid content for the 28 transformants analyzed is 4.3 with a standard deviation of the mean of 0.39. While there are no lines which deviate greatly from the mean in bulk seed analysis, line 130-126 is in exess of 2 standard deviations lower than the mean. Since this could be indicative of a weak antisense phenotype observed in a segregating seed population as described above, 12 single seeds from the plant were analyzed for relative fatty acid content along with 12 single seeds from a non-transformed Westar plant grown in the same growth chamber and planted at a comparable date. The results of those analyses are shown in Table 12.

TABLE 12

The relative contribution of 5 fatty acids to total fatty acid content in single seeds from transformant 130-126 and from single seeds of a non-transformed oontrol plant

| TRANSFORMANT NO. | FATTY ACID AS % OF TOTAL FATTY ACIDS | | | | |
|---|---|---|---|---|---|
| | 16:0 | 18:0 | 18:1 | 18:2 | 18:3 |
| 130-126 | 3.07 | 1.51 | 67.27 | 17.26 | 8.74 |
| 130-126 | 3.11 | 1.74 | 64.70 | 18.19 | 9.47 |
| 130-126 | 3.20 | 1.66 | 69.71 | 16.21 | 7.40 |
| 130-126 | 3.47 | 1.77 | 69.98 | 15.66 | 6.73 |
| 130-126 | 3.76 | 2.04 | 71.26 | 15.42 | 5.00 |
| 130-126 | 3.56 | 1.80 | 71.74 | 15.47 | 4.83 |
| 130-126 | 3.30 | 2.05 | 65.22 | 18.11 | 9.37 |
| 130-126 | 3.45 | 1.91 | 71.32 | 14.72 | 5.94 |
| 130-126 | 4.30 | 1.90 | 64.97 | 17.91 | 8.84 |
| 130-126 | 2.95 | 1.93 | 65.57 | 17.27 | 10.30 |
| 130-126 | 3.44 | 1.71 | 69.98 | 16.06 | 6.26 |
| 130-126 | 3.43 | 1.81 | 72.40 | 14.78 | 5.02 |
| WESTAR4/B | 3.81 | 1.71 | 62.46 | 20.46 | 9.70 |
| WESTAR4/8 | 4.28 | 1.42 | 63.27 | 20.86 | 8.30 |
| WESTAR4/8 | 4.00 | 1.55 | 68.80 | 18.08 | 5.30 |
| WESTAR4/8 | 4.19 | 1.97 | 61.51 | 20.01 | 10.40 |
| WESTAR4/8 | 4.37 | 1.60 | 63.92 | 20.02 | 7.96 |
| WESTAR4/8 | 4.41 | 1.45 | 62.95 | 20.39 | 8.36 |
| WESTAR4/8 | 4.12 | 1.84 | 60.90 | 21.19 | 10.00 |
| WESTAR4/8 | 3.89 | 1.69 | 63.63 | 19.68 | 8.99 |
| WESTAR4/8 | 3.97 | 1.73 | 67.68 | 17.57 | 6.43 |
| WESTAR4/8 | 3.97 | 1.78 | 63.78 | 19.47 | 8.94 |
| WESTAR4/8 | 3.85 | 1.76 | 64.85 | 18.56 | 8.65 |
| WESTAR4/8 | 4.06 | 1.69 | 63.74 | 20.16 | 8.52 |

The mean relative palmitic acid content of the 12 seeds from transformant 130-126 is 3.42% and the standard deviation of the mean is 0.359, while the mean palmitic acid content of the 12 control seeds is 4.08 with a standard deviation of the mean of 0.20. The lower mean, greater standard deviation and wider range of observed palmitic acid contents are all indicative of a segregating population in which the seeds homozygous for the antisense transgene for the canola palmitoyl-ACP thioesterase produce slightly less palmitic acid. The observed phenotype will be confirmed by analysis of bulk seeds from multiple plants in the next generation.

As stated for the sense construction above, the occurrence of maximally altered fatty acid phenotypes are rare transformation events in canola. Thus, the phenotype of the low palmitate segregating seed in transformant 130-126 is indicative that the antisense under expression of palmitoyl-ACP thioesterase in canola seeds is capable of decreasing the production of saturated fatty acids but does not indicate the minimum palmitic acid content which may be achieved by this method.

What is claimed is:

1. An isolated nucleic acid fragment encoding a plant acyl-ACP thioesterase wherein said thioesterase has a preference of at least two-fold for palmitoyl-ACP over either stearoyl-ACP or oleoyl-ACP and further wherein said isolated nucleic acid fragment hybridizes to one of the nucleotide sequences set forth in SEQ ID NOS:1, 2, and 31 under the following set of conditions: hybridization at 60° C. in 6×SCC, 0.1% SDS for 18 hr, washing at 60° C. in 0.2×SSC, 0.1% SDS twice for 10 min each.

2. An isolated nucleic acid fragment encoding the soybean seed acyl-ACP thioesterase encoded by nucleotides 1 to 1688 of SEQ ID NO:1.

3. An isolated nucleic acid fragment encoding the canola seed acyl-ACP thioesterase encoded by nucleotides 1 to 1483 of SEQ ID NO:2.

4. An isolated nucleic acid fragment encoding the canola seed acyl-ACP thioesterase encoded by nucleotides 1 to 1674 of SEQ ID NO:31.

5. An isolated nucleic acid fragment encoding a plant acyl-ACP thioesterase wherein said thioesterase has a preference of at least two-fold for palmitoyl-ACP over either stearoyl-ACP or oleoyl-ACP and further wherein said isolated nucleic acid fragment hybridizes to nucleotides 506 to 1477 of SEQ ID NO:1, nucleotides 255 to 1226 of SEQ ID NO:2, or nucleotides 479 to 1438 of SEQ ID NO:31 under the following set of conditions: hybridization at 60° C. in 6×SCC, 0.1% SDS for 18 hr, washing at 60° C. in 0.2×SSC, 0.1% SDS twice for 10 min each.

6. The isolated nucleic acid fragment of claim 2 wherein the said nucleotide sequence encodes the catalytically active soybean seed palmitoyl-ACP thioesterase enzyme encoded by nucleotides 506 to 1477 of SEQ ID NO:1.

7. The isolated nucleic acid fragment of claim 3 wherein the said nucleotide sequence encodes the catalytically active canola seed palmitoyl-ACP thioesterase enzyme encoded by nucleotides 255 to 1226 of SEQ ID NO:2.

8. The isolated nucleic acid fragment of claim 4 wherein the said nucleotide sequence encodes the catalytically active canola seed palmitoyl-ACP thioesterase enzyme encoded by nucleotides 479 to 1438 of SEQ ID NO:31.

9. An isolated nucleic-acid fragment encoding a soybean acyl-ACP thioesterase having the amino acid sequence of SEQ ID NO:29.

10. An isolated nucleic-acid fragment encoding a rapeseed acyl-ACP thioesterase having the amino acid sequence of SEQ ID NO:30.

11. An isolated nucleic-acid fragment encoding a rapeseed acyl-ACP thioesterase having the amino acid sequence of SEQ ID NO:32.

12. A chimeric gene for transforming a plant of an oil producing species comprising the nucleic acid fragment of claim 1 operably linked in antisense orientation to regulatory sequences, wherein said chimeric gene causes inhibition of expression of palmitoyl-ACP thioesterase in seed of said plant wherein said inhibition results in lower-than-normal levels of saturated fatty acids.

13. A chimeric gene for transforming a plant of an oil producing species comprising the nucleic acid fragment of claim 1 operably linked in sense orientation to regulatory sequences, wherein said chimeric gene causes sense elevation or co-suppression of palmitoyl-ACP thioesterase in seed of said plant.

14. A chimeric gene for transforming a plant of an oil producing species comprising the nucleic acid fragment of claim 2 operably linked in antisense orientation to regulatory sequences, wherein said chimeric gene causes inhibition of expression of palmitoyl-ACP thioesterase in seed of said plant.

15. A chimeric gene for transforming a plant of an oil producing species comprising the nucleic acid fragment of claim 2 operably linked in sense orientation to regulatory sequences, wherein said chimeric gene causes sense elevation or co-suppression of palmitoyl-ACP thioesterase in seed of said plant.

16. A chimeric gene for transforming a plant of an oil producing species comprising the nucleic acid fragment of claim 3 or 4 operably linked in antisense orientation to regulatory sequences, wherein said chimeric gene causes inhibition of expression of palmitoyl-ACP thioesterase in seed of said plant.

17. A chimeric gene for transforming a plant of an oil producing species comprising the nucleic acid fragment of claim 3 or 4 operably linked in sense orientation to regulatory sequences, wherein said chimeric gene causes elevation or co-suppression of palmitoyl-ACP thioesterase in seed of said plant.

18. The chimeric gene of claim 12 wherein said plant of an oil producing species is selected from the group consisting of soybean, rapeseed, sunflower, cotton, cocoa, peanut, safflower, and corn.

19. The chimeric gene of claim 13 wherein said plant of an oil producing species is selected from the group consisting of soybean, rapeseed, sunflower, cotton, cocoa, peanut, safflower, and corn.

20. A plant cell transformed with the chimeric gene of claim 12.

21. A plant cell transformed with the chimeric gene of claim 13.

22. The plant cell, as described in claim 20, wherein the plant cell is selected from the group consisting of soybean, rapeseed, sunflower, cotton, cocoa, peanut, safflower, and corn.

23. The plant cell, as described in claim 21, wherein the plant cell is selected from the group consisting of soybean, rapeseed, sunflower, cotton, cocoa, peanut, safflower, and corn.

24. A method of producing plant seed oil comprising lower-than-normal levels of palmitic and stearic acids comprising:
  (a) transforming plant cells of an oil producing species with the chimeric gene of claim 12 or the chimeric gene of claim 13,
  (b) growing fertile plants from the transformed plant cells obtained from step (a),
  (c) screening progeny seeds from said fertile plants for lower-than-normal levels palmitic and stearic acids, and
  (d) crushing said progeny seeds to obtain said plant seed oil comprising lower-than-normal levels of palmitic and stearic acids.

25. A method of producing plant seed oil comprising higher-than-normal levels of palmitic and stearic acids comprising:
  (a) transforming plant cells of an oil producing species with the chimeric gene of claim 13,
  (b) growing fertile plants from the transformed plant cells obtained from step (a),
  (c) screening progeny seeds from said fertile plants for higher-than-normal levels of palmitic and stearic acids, and
  (d) crushing said progeny seeds to obtain said plant seed oil comprising higher-than-normal levels of palmitic and stearic acids.

26. A method of producing soybean seed oil comprising lower-than-normal levels of palmitic and stearic acids comprising:
  (a) transforming soybean cells with the chimeric gene of claim 14,
  (b) growing fertile soybean plants from the transformed soybean cells obtained from step (a),
  (c) screening progeny seeds from said fertile soybean plants for lower-than-normal levels of palmitic and stearic acids, and
  (d) crushing said progeny seeds to obtain said soybean seed oil comprising lower-than-normal levels of palmitic and stearic acids.

27. A method of producing soybean seed oil comprising higher-than-normal levels of palmitic and stearic acids comprising:
  (a) transforming soybean cells with the chimeric gene of claim 15,
  (b) growing fertile soybean plants from the transformed soybean cells obtained from step (a),
  (c) screening progeny seeds from said fertile soybean plants for higher-than-normal levels of palmitic and stearic acids, and
  (d) crushing said progeny seeds to obtain said soybean seed oil comprising higher-than-normal levels of palmitic and stearic acids.

28. A method of producing rapeseed seed oil comprising lower-than-normal levels of palmitic and stearic acids comprising:
  (a) transforming rapeseed cells with the chimeric gene of claim 16,
  (b) growing fertile rapeseed plants from the transformed rapeseed cells obtained from step (a),
  (c) screening progeny seeds from said fertile rapeseed plants for lower-than-normal levels of palmitic and stearic acids, and
  (d) crushing said progeny seeds to obtain said rapeseed seed oil comprising lower-than-normal levels of palmitic and stearic acids.

29. A method of producing rapeseed seed oil comprising higher-than-normal levels of palmitic and stearic acids comprising:
  (a) transforming rapeseed cells with the chimeric gene of claim 17,
  (b) growing fertile rapeseed plants from the transformed rapeseed cells obtained from step (a),
  (c) screening progeny seeds from said fertile rapeseed plants for higher-than-normal levels of palmitic and stearic acids, and
  (d) crushing said progeny seeds to obtain said rapeseed seed oil comprising higher-than-normal levels of palmitic and stearic acids.

30. The method of claim 24 wherein the plant cells are from an oil producing species selected from the group consisting of soybean, rapeseed, sunflower, cotton, cocoa, peanut, safflower, and corn.

31. The method of claim 25 wherein the plant cells are from an oil producing species selected from the group consisting of soybean, rapeseed, sunflower, cotton, cocoa, peanut, safflower, and corn.

32. The method of claim 24 wherein the transforming of step (a) is accomplished by a process selected from the group consisting of Agrobacterium infection, electroporation, and high-velocity ballistic bombardment.

33. The method of claim 25 wherein the transforming of step (a) is accomplished by a process selected from the group consisting of Agrobacterium infection, electroporation, and high-velocity ballistic bombardment.

* * * * *